(12) United States Patent
Porchia et al.

(10) Patent No.: US 7,503,668 B2
(45) Date of Patent: Mar. 17, 2009

(54) DEVICE PROVIDING COORDINATED EMISSION OF LIGHT AND VOLATILE ACTIVE

(75) Inventors: Jose Porchia, Greenfield, WI (US); Jeffrey J. Wolf, Racine, WI (US); David C. Belongia, Kewaskum, WI (US); Kara J. Mackey, Milwaukee, WI (US); Mark Niederberger, Einsiedeln (CH); Thomas Froehlich, Zurich (CH)

(73) Assignee: S.C. Johnson & Son, Inc., Racine, WI (US)

( * ) Notice: Subject to any disclaimer, the term of this patent is extended or adjusted under 35 U.S.C. 154(b) by 11 days.

(21) Appl. No.: 11/050,242

(22) Filed: Feb. 3, 2005

(65) Prior Publication Data

US 2005/0169666 A1    Aug. 4, 2005

Related U.S. Application Data

(60) Provisional application No. 60/541,067, filed on Feb. 3, 2004.

(51) Int. Cl.
*F21L 19/00* (2006.01)
(52) U.S. Cl. .................. 362/161; 362/252; 422/123
(58) Field of Classification Search ............. 362/161, 362/157, 166, 167, 810, 643; 422/123
See application file for complete search history.

(56) References Cited

U.S. PATENT DOCUMENTS

| | | |
|---|---|---|
| 240,764 A | 4/1881 | Reynolds |
| D27,883 S | 11/1897 | Noke |
| 606,850 A | 7/1898 | Wallace et al. |
| 738,999 A | 9/1903 | Higgins |
| 937,836 A | 10/1909 | Matthai |
| D42,648 S | 6/1912 | Sanford |
| D55,864 S | 7/1920 | Jenkins |
| 1,648,748 A | 11/1927 | Traub |
| 1,665,412 A | 4/1928 | Hall |
| D75,124 S | 5/1928 | Jenkins |

(Continued)

FOREIGN PATENT DOCUMENTS

AU    4932300    11/2000

(Continued)

OTHER PUBLICATIONS

International Search Report and Written Opinion dated Apr. 20, 2007, Appl. No. PCT/US06/042919.

(Continued)

*Primary Examiner*—Ali Alavi
*Assistant Examiner*—Evan Dzierzynski

(57) ABSTRACT

A flameless candle that releases a volatile active includes at least one LED positioned in a tip (106), a cartridge mount (128), and a support structure (102, 141). The at least one LED emits a flickering light that emulates a flame of a candle. The cartridge mount (128) receives and secures a replaceable cartridge (104*a*) containing a volatile active to be released into the atmosphere over time. The support structure (120, 141) supports the at least one LED and the cartridge mount (128). The support structure (120, 141) is configured to allow airflow across the replaceable cartridge (104*a*) when the replaceable cartridge (104*a*) is mounted in the cartridge mount (128).

30 Claims, 11 Drawing Sheets

U.S. PATENT DOCUMENTS

| | | | |
|---|---|---|---|
| 1,806,046 A | 5/1931 | Deeter | |
| 1,947,806 A | 2/1934 | Smith | |
| 1,975,496 A | 10/1934 | Barrett, Jr. | |
| 2,014,217 A | 9/1935 | Williamson | |
| D103,209 S | 2/1937 | Beiser | |
| 2,080,259 A | 5/1937 | Frie, Jr. | |
| RE20,434 E | 7/1937 | Barrett, Jr. | |
| 2,102,224 A | 12/1937 | Ruppel | |
| 2,111,642 A | 3/1938 | Saier | |
| 2,124,009 A | 7/1938 | Schneider | |
| D128,935 S | 8/1941 | Derham et al. | |
| 2,254,134 A | 8/1941 | Berry | |
| 2,360,603 A | 10/1944 | Ward | |
| 2,435,756 A | 2/1948 | Schlesinger | 21/120 |
| 2,435,811 A | 2/1948 | Waters | 362/569 |
| 2,437,809 A | 3/1948 | Engelbrecht | |
| 2,459,898 A | 1/1949 | Stiffel | |
| 2,494,995 A | 1/1950 | Gardner | |
| 2,523,818 A | 9/1950 | Cortes | |
| 2,525,464 A | 10/1950 | Springer | |
| 2,557,501 A | 6/1951 | Fusay et al. | 422/125 |
| 2,567,780 A | 9/1951 | Oppelt | |
| 2,608,645 A | 8/1952 | Hines | |
| 2,611,068 A | 9/1952 | Wellens | |
| 2,632,098 A | 3/1953 | Marchese | |
| 2,691,548 A | 10/1954 | Feucht et al. | |
| 2,721,244 A | 10/1955 | Seekins | |
| D180,916 S | 9/1957 | Perlman | |
| 2,807,691 A | 9/1957 | Sorenson | |
| 2,863,547 A | 12/1958 | Cavalleri | |
| 2,935,608 A | 5/1960 | Mirzwinski | |
| 2,954,771 A | 10/1960 | Boyan | |
| 2,984,724 A | 5/1961 | Merz | |
| D191,396 S | 9/1961 | Weber, III | |
| 3,045,878 A | 7/1962 | Blanford et al. | |
| 3,080,624 A | 3/1963 | Weber, III | 422/125 |
| 3,145,323 A | 8/1964 | Klotz | |
| 3,149,761 A | 9/1964 | Harris et al. | |
| 3,153,123 A | 10/1964 | Harman | |
| 3,174,659 A | 3/1965 | Sorber et al. | |
| 3,209,949 A | 10/1965 | Gurtler | |
| 3,233,093 A | 2/1966 | Gerlat | |
| D205,556 S | 8/1966 | Plochman, Jr. | |
| 3,428,224 A | 2/1969 | Eberhardt et al. | |
| 3,429,484 A | 2/1969 | Baldwin | |
| 3,435,286 A | 3/1969 | Kayatt | |
| D214,831 S | 8/1969 | Lomont et al. | |
| 3,473,014 A | 10/1969 | Kayne | |
| 3,500,126 A | 3/1970 | Ford | 315/209 |
| 3,506,876 A | 4/1970 | Antonich | |
| D217,719 S | 6/1970 | McNair et al. | |
| D218,145 S | 7/1970 | Doblin | |
| 3,531,637 A | 9/1970 | Nathanson | |
| 3,580,432 A | 5/1971 | Brooks | |
| D221,891 S | 9/1971 | Douglas | |
| 3,604,920 A | 9/1971 | Niles | |
| 3,648,905 A | 3/1972 | Kauder | |
| 3,710,182 A | 1/1973 | Van Reenen | |
| 3,748,464 A | 7/1973 | Andeweg | 362/355 |
| 3,749,904 A | 7/1973 | Graff | 362/265 |
| 3,761,702 A | 9/1973 | Andeweg | 362/161 |
| 3,789,211 A | 1/1974 | Kramer | 240/102 |
| 3,860,847 A | 1/1975 | Carley | |
| 3,890,085 A | 6/1975 | Andeweg | 431/125 |
| 3,893,041 A | 7/1975 | Foster et al. | |
| 3,923,458 A | 12/1975 | Moran | 422/306 |
| 3,926,655 A | 12/1975 | Miles | |
| 3,934,105 A | 1/1976 | Lockard | |
| 3,943,352 A | 3/1976 | Pena May | |
| 3,944,806 A | 3/1976 | Jones et al. | |
| 3,946,173 A | 3/1976 | Haber | |
| 3,948,445 A | 4/1976 | Andeweg | 239/53 |
| 3,987,942 A | 10/1976 | Morane et al. | |
| 3,990,848 A | 11/1976 | Corris | |
| D243,017 S | 1/1977 | Fossella | |
| 4,017,729 A | 4/1977 | Frazier, Jr. | |
| 4,035,451 A | 7/1977 | Tringali | 261/101 |
| 4,038,561 A | 7/1977 | Lorenz | |
| 4,052,622 A | 10/1977 | Lorenz | |
| 4,064,414 A | 12/1977 | Bergeson et al. | 315/208 |
| 4,071,805 A | 1/1978 | Brock | |
| 4,077,549 A | 3/1978 | Beard | |
| 4,111,655 A | 9/1978 | Quincey | |
| 4,132,359 A | 1/1979 | Nozawa | |
| 4,159,442 A | 6/1979 | Komatsu | |
| 4,177,407 A | 12/1979 | Goldstein et al. | |
| 4,187,532 A | 2/1980 | Naffier | |
| 4,228,885 A | 10/1980 | Cavalleri | |
| 4,253,045 A | 2/1981 | Weber | |
| 4,264,037 A | 4/1981 | Nozawa | |
| 4,276,236 A | 6/1981 | Sullivan et al. | |
| 4,283,661 A | 8/1981 | Doty | |
| 4,307,460 A | 12/1981 | Polonsky | |
| 4,325,110 A | 4/1982 | Tang | |
| 4,328,534 A | 5/1982 | Abe | |
| 4,346,059 A | 8/1982 | Spector | 422/125 |
| 4,413,779 A | 11/1983 | Santini | |
| 4,417,182 A | 11/1983 | Weber | |
| 4,477,249 A | 10/1984 | Ruzek et al. | |
| 4,492,896 A | 1/1985 | Jullien | 315/153 |
| 4,493,011 A | 1/1985 | Spector | 362/96 |
| 4,500,795 A | 2/1985 | Hochstein et al. | |
| 4,502,630 A | 3/1985 | Haworth et al. | |
| 4,508,520 A | 4/1985 | Sellers et al. | |
| 4,510,556 A * | 4/1985 | Johnson | 362/184 |
| 4,540,984 A | 9/1985 | Waldman | |
| 4,550,363 A | 10/1985 | Sandell | |
| 4,558,820 A | 12/1985 | Harris, Jr. | |
| D282,152 S | 1/1986 | Mendenhall | |
| 4,568,269 A | 2/1986 | Lin | |
| 4,583,686 A | 4/1986 | Martens et al. | |
| 4,588,874 A | 5/1986 | Napierski | |
| 4,593,232 A | 6/1986 | McEdwards | 315/199 |
| 4,598,198 A | 7/1986 | Fayfield | 250/205 |
| 4,617,614 A | 10/1986 | Lederer | 362/212 |
| 4,621,768 A | 11/1986 | Lhoste et al. | |
| 4,629,604 A | 12/1986 | Spector | |
| D287,885 S | 1/1987 | Bolduc | |
| D288,856 S | 3/1987 | Owen et al. | |
| 4,660,763 A | 4/1987 | Gutkowski et al. | |
| 4,660,764 A | 4/1987 | Joyaux et al. | |
| 4,666,638 A | 5/1987 | Baker et al. | |
| 4,675,578 A | 6/1987 | Mitchell et al. | |
| D291,242 S | 8/1987 | Harden et al. | |
| 4,693,681 A | 9/1987 | Comstock | |
| 4,695,435 A | 9/1987 | Spector | |
| 4,695,439 A | 9/1987 | Ritsko et al. | |
| 4,707,338 A | 11/1987 | Spector | |
| 4,714,984 A | 12/1987 | Spector | |
| 4,739,928 A | 4/1988 | O'Neil | |
| 4,743,406 A | 5/1988 | Steiner et al. | |
| 4,768,393 A | 9/1988 | Beaman | |
| 4,771,769 A | 9/1988 | Hegemann et al. | |
| 4,773,571 A | 9/1988 | Hagan et al. | |
| 4,777,345 A | 10/1988 | Manchester | |
| 4,779,734 A | 10/1988 | Kydonieus | |
| 4,781,895 A | 11/1988 | Spector | |
| 4,804,323 A | 2/1989 | Kim | |
| 4,804,821 A | 2/1989 | Glucksman | |
| 4,805,839 A | 2/1989 | Malek | |
| D300,107 S | 3/1989 | Trombly | |
| D301,205 S | 5/1989 | Joyaux et al. | |
| 4,826,054 A | 5/1989 | Frutin | |
| 4,830,791 A | 5/1989 | Muderlak et al. | 261/26 |

| Patent No. | Date | Name | Ref |
|---|---|---|---|
| 4,837,421 A | 6/1989 | Luthy | |
| 4,839,780 A | 6/1989 | Chuan et al. | |
| 4,840,770 A | 6/1989 | Walz et al. | |
| 4,849,606 A | 7/1989 | Martens, III et al. | |
| 4,857,240 A | 8/1989 | Kearnes et al. | |
| 4,865,816 A | 9/1989 | Walz et al. | |
| 4,866,580 A | 9/1989 | Blackerby | 362/205 |
| 4,870,325 A | 9/1989 | Kazar | |
| 4,895,512 A | 1/1990 | Sullivan et al. | |
| 4,901,891 A | 2/1990 | Gonclaves | |
| 4,913,315 A | 4/1990 | Purzycki | 221/200 |
| 4,913,350 A | 4/1990 | Purzycki | |
| 4,926,298 A | 5/1990 | Zimmerman | |
| 4,931,224 A | 6/1990 | Holzner, Sr. | |
| 4,960,240 A | 10/1990 | McElfresh | |
| 4,963,939 A | 10/1990 | Kurando et al. | 355/260 |
| 4,968,487 A | 11/1990 | Yamamoto et al. | |
| D314,237 S | 1/1991 | Blumanthal, Jr. | |
| 4,983,119 A | 1/1991 | Lin | |
| 4,992,912 A | 2/1991 | Lee | |
| D317,059 S | 5/1991 | Menter | |
| 5,013,972 A | 5/1991 | Malkieli et al. | 315/209 |
| 5,015,175 A | 5/1991 | Lee | |
| 5,018,647 A | 5/1991 | Abplanalf | |
| 5,032,766 A | 7/1991 | Gundlach et al. | |
| 5,034,658 A | 7/1991 | Hiering et al. | |
| 5,035,728 A | 7/1991 | Fang | |
| 5,038,972 A | 8/1991 | Muderlak et al. | |
| 5,040,705 A | 8/1991 | Snell | |
| 5,050,798 A | 9/1991 | Sullivan | |
| 5,057,003 A | 10/1991 | Yang | |
| D321,476 S | 11/1991 | Alcover | |
| 5,069,876 A | 12/1991 | Oshinsky | |
| 5,091,678 A | 2/1992 | Chin-Song | |
| RE33,864 E | 3/1992 | Steiner et al. | 261/30 |
| 5,097,180 A | 3/1992 | Ignon et al. | 315/200 A |
| D326,168 S | 5/1992 | Smith | |
| 5,111,477 A | 5/1992 | Muderlak | |
| 5,114,625 A | 5/1992 | Gibson | |
| 5,115,975 A | 5/1992 | Shilling | 239/55 |
| 5,126,078 A | 6/1992 | Steiner et al. | |
| 5,133,042 A | 7/1992 | Pelonis | |
| 5,138,538 A | 8/1992 | Sperling | |
| 5,147,582 A | 9/1992 | Holzner, Sr. et al. | |
| 5,148,984 A | 9/1992 | Bryson, Jr. et al. | 239/58 |
| 5,152,602 A | 10/1992 | Boschetto | 362/276 |
| 5,164,636 A | 11/1992 | Allaire | |
| 5,174,645 A | 12/1992 | Chung | |
| 5,175,791 A | 12/1992 | Muderlak et al. | |
| 5,178,450 A | 1/1993 | Zelensky et al. | |
| 5,187,655 A | 2/1993 | Post et al. | |
| D333,778 S | 3/1993 | Magidson et al. | |
| 5,212,672 A | 5/1993 | Loisch et al. | |
| 5,217,696 A | 6/1993 | Wolverton et al. | 422/121 |
| 5,223,182 A | 6/1993 | Steiner et al. | |
| 5,228,771 A | 7/1993 | Zimmerman | |
| 5,234,162 A | 8/1993 | Sullivan | |
| 5,249,713 A | 10/1993 | Reich et al. | |
| 5,316,185 A | 5/1994 | Meenan | |
| D349,642 S | 8/1994 | Abfier | |
| 5,342,584 A | 8/1994 | Fritz et al. | |
| 5,364,027 A | 11/1994 | Kuhn | |
| D353,194 S | 12/1994 | Walton et al. | |
| 5,370,313 A | 12/1994 | Beard | |
| 5,370,829 A | 12/1994 | Kunze | |
| 5,376,338 A | 12/1994 | Zlotnik | |
| RE34,847 E | 2/1995 | Muderlak et al. | |
| 5,388,714 A | 2/1995 | Zutler | |
| 5,392,379 A | 2/1995 | Fussell | |
| D356,523 S | 3/1995 | Rahr | |
| D357,085 S | 4/1995 | Ratia | |
| D357,531 S | 4/1995 | Weick | |
| D359,346 S | 6/1995 | Martin | |
| 5,424,927 A * | 6/1995 | Schaller et al. | 362/157 |
| 5,460,787 A | 10/1995 | Colon | |
| 5,498,397 A | 3/1996 | Horng | 422/124 |
| 5,547,616 A | 8/1996 | Dancs et al. | |
| 5,564,665 A | 10/1996 | Resnick | |
| 5,600,209 A | 2/1997 | St. Louis | |
| 5,611,486 A | 3/1997 | Paul | |
| D378,802 S | 4/1997 | Corcoran | |
| D380,257 S | 6/1997 | Ganor | |
| D380,821 S | 7/1997 | Chen | |
| D381,561 S | 7/1997 | Manca | |
| 5,647,053 A | 7/1997 | Schroeder et al. | |
| 5,651,942 A | 7/1997 | Christensen | 422/125 |
| 5,662,835 A | 9/1997 | Collingwood | |
| D386,974 S | 12/1997 | Wefler | |
| D387,447 S | 12/1997 | Hollington | |
| 5,697,695 A | 12/1997 | Lin et al. | |
| D388,892 S | 1/1998 | Ratia | |
| D390,941 S | 2/1998 | Cessaroni et al. | |
| D392,032 S | 3/1998 | Zaragoza et al. | |
| 5,725,152 A | 3/1998 | Akyu | |
| 5,782,553 A | 7/1998 | McDermott | |
| 5,788,061 A | 8/1998 | Hammond | |
| 5,788,155 A | 8/1998 | Martin et al. | 239/34 |
| 5,788,931 A | 8/1998 | Muñoz Quintana | 422/125 |
| 5,791,774 A | 8/1998 | Briles | |
| 5,805,768 A | 9/1998 | Schwartz et al. | |
| 5,842,763 A | 12/1998 | Lakosky | |
| 5,847,512 A | 12/1998 | Baba et al. | |
| 5,853,672 A | 12/1998 | Lorman et al. | |
| 5,863,108 A | 1/1999 | Lederer | 362/186 |
| D406,365 S | 3/1999 | Furner | |
| 5,884,808 A | 3/1999 | Muderlak et al. | 222/23 |
| 5,890,633 A | 4/1999 | Skillin et al. | |
| 5,891,400 A | 4/1999 | Ansari et al. | 422/125 |
| 5,894,201 A | 4/1999 | Wong | |
| 5,909,845 A | 6/1999 | Greatbatch et al. | |
| 5,909,954 A | 6/1999 | Thomas | |
| 5,924,784 A | 7/1999 | Chliwnyj | 362/234 |
| 5,950,922 A | 9/1999 | Flinn | |
| 5,961,043 A | 10/1999 | Samuelson et al. | |
| 5,964,519 A | 10/1999 | Chun-Ying | |
| 5,969,479 A | 10/1999 | Wong | |
| 5,970,643 A | 10/1999 | Gawel, Jr. | |
| 5,972,290 A | 10/1999 | De Sousa | |
| D416,098 S | 11/1999 | Sher | |
| 5,975,427 A | 11/1999 | Harries | |
| 5,980,064 A | 11/1999 | Metroyanis | 362/194 |
| 5,992,707 A | 11/1999 | Gaichuk | |
| 6,017,139 A | 1/2000 | Lederer | 362/394 |
| D420,754 S | 2/2000 | Huang | |
| 6,030,108 A | 2/2000 | Ishiharada et al. | |
| D422,101 S | 3/2000 | Barraclough et al. | |
| 6,050,551 A | 4/2000 | Anderson | |
| 6,064,357 A | 5/2000 | Okuda | 345/82 |
| 6,066,924 A | 5/2000 | Lederer | 315/185 R |
| D426,667 S | 6/2000 | Kaviani | |
| 6,104,866 A | 8/2000 | DeWitt et al. | |
| 6,104,867 A | 8/2000 | Stathakis et al. | |
| 6,106,786 A | 8/2000 | Akahashi | 422/124 |
| 6,135,612 A | 10/2000 | Clore | 362/184 |
| 6,152,568 A | 11/2000 | Baba et al. | |
| 6,153,981 A | 11/2000 | Thomas et al. | |
| D436,038 S | 1/2001 | Ruiz de Gopegui | |
| D437,040 S | 1/2001 | Soller et al. | |
| D437,064 S | 1/2001 | Boss | |
| 6,196,706 B1 | 3/2001 | Cutts | 362/392 |
| RE37,168 E | 5/2001 | St. Louis | |
| 6,241,362 B1 | 6/2001 | Morrison | 362/231 |
| D448,097 S | 9/2001 | Bodum | |
| D448,535 S | 9/2001 | Delmerico | |
| 6,288,498 B1 | 9/2001 | Cheng | 315/185 S |
| 6,293,474 B1 | 9/2001 | Helf et al. | |

| | | | |
|---|---|---|---|
| D449,877 S | 10/2001 | Delmenico et al. | |
| 6,296,196 B1 | 10/2001 | Denen et al. | |
| 6,302,559 B1 | 10/2001 | Warren | 362/226 |
| 6,305,820 B1 | 10/2001 | Poon | 362/186 |
| D450,862 S | 11/2001 | Alcedo | |
| D451,183 S | 11/2001 | Hirano et al. | |
| 6,325,256 B1 | 12/2001 | Liljeqvist et al. | |
| 6,341,732 B1 | 1/2002 | Martin et al. | |
| 6,351,079 B1 | 2/2002 | Willis | |
| D454,190 S | 3/2002 | Trocola | |
| 6,354,710 B1 | 3/2002 | Nacouzi | 362/96 |
| 6,357,726 B1 | 3/2002 | Watkins | |
| 6,361,192 B1 | 3/2002 | Fussell et al. | 362/331 |
| 6,361,752 B1 | 3/2002 | Demarest et al. | |
| 6,371,450 B1 | 4/2002 | Davis et al. | |
| 6,382,522 B2 | 5/2002 | Tomkins et al. | |
| 6,394,630 B1 | 5/2002 | Skidmore et al. | |
| D460,894 S | 7/2002 | Ziegenfus et al. | |
| 6,446,583 B2 | 9/2002 | Vieira | |
| 6,450,419 B1 | 9/2002 | Martens, III et al. | |
| 6,454,425 B1 | 9/2002 | Lin | 362/96 |
| 6,474,510 B2 | 11/2002 | Frutin | |
| 6,481,639 B1 | 11/2002 | Pozzo | |
| 6,486,726 B1 | 11/2002 | Worley, Sr. et al. | 327/514 |
| 6,487,367 B2 | 11/2002 | Vieira | 392/395 |
| 6,494,349 B1 | 12/2002 | Thompson et al. | |
| 6,501,906 B2 | 12/2002 | Vieira | |
| 6,502,762 B2 * | 1/2003 | Tuttobene, Jr. | 239/59 |
| D470,077 S | 2/2003 | Osawa | |
| D470,433 S | 2/2003 | Osawa | |
| 6,525,487 B2 | 2/2003 | Wei | |
| 6,533,828 B1 | 3/2003 | Calzada | |
| 6,536,746 B2 | 3/2003 | Watkins | |
| 6,540,153 B1 | 4/2003 | Ivri | |
| 6,554,201 B2 | 4/2003 | Klimowicz et al. | |
| 6,555,068 B2 | 4/2003 | Smith | |
| 6,556,147 B1 | 4/2003 | Fisher et al. | 340/908 |
| D474,854 S | 5/2003 | Lam | |
| 6,563,091 B2 | 5/2003 | Vieira | |
| 6,565,012 B1 | 5/2003 | Zaragoza et al. | |
| 6,569,387 B1 | 5/2003 | Furner et al. | |
| D476,070 S | 6/2003 | Millan | |
| 6,572,365 B1 | 6/2003 | Byxbe | |
| 6,575,613 B2 | 6/2003 | Brown et al. | 362/565 |
| 6,581,915 B2 | 6/2003 | Bartsch et al. | |
| D477,095 S | 7/2003 | Avital | |
| D477,424 S | 7/2003 | Avital | |
| 6,584,986 B2 | 7/2003 | Gindi | |
| 6,592,104 B2 | 7/2003 | Cox | |
| 6,595,676 B2 | 7/2003 | Starry | 362/569 |
| 6,610,121 B2 | 8/2003 | Chasen | |
| 6,610,254 B1 | 8/2003 | Furner et al. | |
| 6,616,308 B2 * | 9/2003 | Jensen et al. | 362/351 |
| 6,631,852 B1 | 10/2003 | O'Leary | |
| 6,631,888 B1 | 10/2003 | Prueter | |
| 6,637,627 B1 | 10/2003 | Liljeqvist et al. | |
| D482,465 S | 11/2003 | Slomowitz | |
| 6,646,491 B2 | 11/2003 | Worley, Sr. et al. | |
| 6,655,604 B2 | 12/2003 | Tuttobene, Jr. | |
| 6,659,301 B2 | 12/2003 | Fellows et al. | |
| 6,661,967 B2 | 12/2003 | Levine et al. | |
| D485,624 S | 1/2004 | Kitamura | |
| 6,672,742 B2 | 1/2004 | Alley | |
| 6,685,064 B2 | 2/2004 | Frutin | |
| 6,685,335 B1 | 2/2004 | Yeh et al. | 362/184 |
| 6,685,345 B1 | 2/2004 | Velasquez | 362/394 |
| 6,688,752 B2 | 2/2004 | Moore | 362/234 |
| 6,705,494 B2 | 3/2004 | Thompson et al. | |
| 6,705,541 B2 | 3/2004 | Schuehrer et al. | |
| 6,706,988 B1 | 3/2004 | Helf et al. | |
| 6,712,493 B2 | 3/2004 | Tell et al. | |
| D488,582 S | 4/2004 | Connelly et al. | |
| 6,719,217 B1 | 4/2004 | Tawara et al. | |
| 6,719,443 B2 | 4/2004 | Gutstein et al. | 362/392 |
| 6,728,478 B2 | 4/2004 | Cox et al. | |
| D489,970 S | 5/2004 | Nelson et al. | |
| 6,729,748 B2 | 5/2004 | Reilly | 362/392 |
| 6,741,042 B1 | 5/2004 | Tang | |
| D490,699 S | 6/2004 | Nelson et al. | |
| D492,443 S | 6/2004 | Smith et al. | |
| 6,768,865 B2 | 7/2004 | Stathakis et al. | |
| 6,779,905 B1 | 8/2004 | Mazursky et al. | |
| 6,782,194 B2 | 8/2004 | Schneiderbauer | |
| 6,783,081 B2 | 8/2004 | Pedrotti et al. | 239/136 |
| 6,783,117 B2 | 8/2004 | Wohrle | |
| D495,819 S | 9/2004 | Krieger et al. | |
| 6,786,474 B2 | 9/2004 | Watkins et al. | |
| 6,790,408 B2 | 9/2004 | Whitby et al. | 422/4 |
| 6,792,199 B2 | 9/2004 | Levine et al. | |
| 6,793,149 B2 | 9/2004 | Schramm et al. | |
| 6,799,730 B2 | 10/2004 | Peng et al. | |
| 6,801,003 B2 | 10/2004 | Schanberger et al. | |
| 6,805,301 B2 | 10/2004 | Garcia | |
| 6,808,297 B2 | 10/2004 | Jensen et al. | |
| D497,808 S | 11/2004 | Morris et al. | |
| 6,820,777 B2 | 11/2004 | Frutin | |
| 6,834,847 B2 | 12/2004 | Bartsch et al. | |
| 6,843,430 B2 | 1/2005 | Boticki et al. | |
| 6,854,208 B1 | 2/2005 | Chuang et al. | |
| 6,854,661 B2 | 2/2005 | Monitto | |
| 6,880,958 B2 | 4/2005 | Swarovski | |
| 6,906,472 B2 | 6/2005 | Wong | |
| 6,913,205 B2 | 7/2005 | Cornet et al. | |
| 6,913,733 B2 | 7/2005 | Hardy et al. | |
| 6,926,423 B2 | 8/2005 | Bucher et al. | |
| 6,932,496 B2 | 8/2005 | Rizkin et al. | |
| 6,935,760 B2 | 8/2005 | Bar-Cohen | |
| D509,893 S | 9/2005 | Sevy | |
| 6,957,779 B2 | 10/2005 | Joshi et al. | |
| 6,963,180 B2 | 11/2005 | Rose | |
| 6,971,779 B2 | 12/2005 | Tau et al. | |
| 6,978,941 B2 | 12/2005 | Litherland et al. | |
| 6,983,747 B2 | 1/2006 | Gallem et al. | |
| 6,994,328 B2 | 2/2006 | Watkins et al. | |
| 7,011,426 B2 | 3/2006 | Gabor | |
| 7,011,795 B2 * | 3/2006 | Thompson et al. | 422/125 |
| 7,014,819 B2 | 3/2006 | Hart et al. | |
| 7,067,772 B2 | 6/2006 | Tanner et al. | |
| RE39,204 E | 7/2006 | Hurry et al. | |
| 7,082,259 B2 | 7/2006 | Zobele | |
| 7,086,607 B2 | 8/2006 | Bresolin et al. | |
| 7,098,600 B2 | 8/2006 | Li et al. | |
| 7,114,821 B2 | 10/2006 | Currie et al. | |
| 7,125,142 B2 | 10/2006 | Wainwright | |
| 2002/0066798 A1 | 6/2002 | Laudamiel-Pellet et al. | |
| 2002/0068009 A1 | 6/2002 | Laudamiel-Pellet et al. | |
| 2002/0068010 A1 | 6/2002 | Laudamiel-Pellet et al. | |
| 2002/0080601 A1 | 6/2002 | Meltzer | 362/96 |
| 2002/0093834 A1 | 7/2002 | Yu et al. | 362/565 |
| 2002/0136886 A1 | 9/2002 | He et al. | |
| 2002/0158351 A1 | 10/2002 | Wohrle | 261/142 |
| 2003/0007887 A1 * | 1/2003 | Roumpos et al. | 422/1 |
| 2003/0053305 A1 | 3/2003 | Lin | |
| 2003/0081420 A1 | 5/2003 | Jensen et al. | 362/392 |
| 2003/0137258 A1 | 7/2003 | Piepgras et al. | |
| 2003/0162142 A1 | 8/2003 | Bennetts et al. | |
| 2003/0175148 A1 | 9/2003 | Kvietok et al. | |
| 2003/0189825 A1 | 10/2003 | Tauch et al. | |
| 2003/0198045 A1 * | 10/2003 | Kitchen | 362/235 |
| 2003/0210555 A1 | 11/2003 | Cicero et al. | 362/555 |
| 2003/0214259 A9 | 11/2003 | Dowling et al. | 315/312 |
| 2003/0227265 A1 | 12/2003 | Biebl | |
| 2004/0007887 A1 | 1/2004 | Kvietok et al. | |
| 2004/0009103 A1 | 1/2004 | Westring | 422/125 |
| 2004/0019818 A1 | 1/2004 | Murdell et al. | |
| 2004/0028551 A1 | 2/2004 | Kvietok et al. | |

| | | | |
|---|---|---|---|
| 2004/0032733 A1 | 2/2004 | Gabriel et al. | |
| 2004/0033067 A1* | 2/2004 | He et al. | 392/395 |
| 2004/0033171 A1 | 2/2004 | Kvietok et al. | |
| 2004/0037069 A1 | 2/2004 | Blackbourn | 362/161 |
| 2004/0050948 A1 | 3/2004 | Bartels | |
| 2004/0051474 A1 | 3/2004 | Wong | 315/291 |
| 2004/0094636 A1 | 5/2004 | Channer | |
| 2004/0141315 A1 | 7/2004 | Sherburne | 362/161 |
| 2004/0160196 A1 | 8/2004 | Wong | 315/291 |
| 2004/0179355 A1 | 9/2004 | Gabor | 362/161 |
| 2004/0196658 A1 | 10/2004 | Fung | 362/392 |
| 2004/0200907 A1 | 10/2004 | Martens et al. | |
| 2004/0222245 A1 | 11/2004 | Marroncles | |
| 2004/0222246 A1 | 11/2004 | Bates et al. | |
| 2004/0246711 A1 | 12/2004 | Brenchley et al. | |
| 2004/0252498 A1 | 12/2004 | Gustein et al. | |
| 2004/0257798 A1* | 12/2004 | Hart et al. | 362/96 |
| 2004/0262418 A1 | 12/2004 | Smith et al. | |
| 2004/0262421 A1 | 12/2004 | Hurry et al. | |
| 2004/0264169 A1* | 12/2004 | Limburg et al. | 362/96 |
| 2005/0045664 A1 | 3/2005 | Taylor | |
| 2005/0047127 A1 | 3/2005 | Tutman | 362/205 |
| 2005/0053368 A1 | 3/2005 | Pesu et al. | |
| 2005/0074358 A1 | 4/2005 | Hart et al. | |
| 2005/0089316 A1 | 4/2005 | He et al. | |
| 2005/0111217 A1 | 5/2005 | Feng | |
| 2005/0116059 A1 | 6/2005 | Lin | |
| 2005/0166945 A1 | 8/2005 | Whitmore | |
| 2005/0169666 A1 | 8/2005 | Porchia et al. | |
| 2005/0169812 A1 | 8/2005 | Helf et al. | |
| 2005/0184045 A1 | 8/2005 | Shimizu et al. | |
| 2005/0184168 A1 | 8/2005 | Peng | |
| 2005/0185392 A1* | 8/2005 | Walter et al. | 362/96 |
| 2005/0196716 A1 | 9/2005 | Haab et al. | |
| 2005/0226788 A1 | 10/2005 | Hrybyk et al. | |
| 2005/0230495 A1 | 10/2005 | Feriani et al. | |
| 2005/0254248 A1 | 11/2005 | Lederer | |
| 2006/0039137 A1 | 2/2006 | Lederer | |
| 2006/0119287 A1 | 6/2006 | Campbell et al. | |
| 2006/0125420 A1 | 6/2006 | Boone et al. | |
| 2006/0175426 A1 | 8/2006 | Schramm et al. | |
| 2006/0177786 A1 | 8/2006 | Hu | |
| 2006/0208666 A1 | 9/2006 | Johnson | |
| 2006/0221617 A1 | 10/2006 | Chien | |
| 2007/0053181 A1 | 3/2007 | Urkumyan | |
| 2007/0056837 A1 | 3/2007 | Chiu | |
| 2007/0154857 A1 | 7/2007 | Cho | |
| 2007/0177393 A1 | 8/2007 | Hirata | |

FOREIGN PATENT DOCUMENTS

| | | |
|---|---|---|
| DE | 297 13 945 U1 | 10/1997 |
| DE | 297 13 945 | 11/1997 |
| DE | 201 03 621 U1 | 5/2001 |
| DE | 201 03 621 | 6/2001 |
| EP | 1281406 A1 | 2/2003 |
| FR | 2628825 | 9/1989 |
| GB | 2067368 | 7/1981 |
| GB | 2239306 | 6/1991 |
| GB | 2 347 563 | 9/2000 |
| GB | 2 388 653 | 11/2003 |
| GB | 2 398 627 | 8/2004 |
| GB | 2 398 627 A | 8/2004 |
| JP | 5 408 2864 | 7/1979 |
| JP | 01-243483 | 9/1989 |
| JP | 4 122 415 | 4/1992 |
| JP | 06052709 | 2/1994 |
| JP | 09106890 | 4/1997 |
| JP | 09-201155 | 8/1997 |
| JP | 9-244575 | 9/1997 |
| JP | 9-007411 | 10/1997 |
| JP | 11086602 | 3/1999 |
| JP | 2000245617 | 9/2000 |
| JP | 2002270013 | 9/2002 |
| JP | 2003187615 | 7/2003 |
| WO | WO 99/17717 | 4/1999 |
| WO | WO 00/64498 | 11/2000 |
| WO | WO 03/068413 | 8/2003 |
| WO | WO 2005/097348 | 10/2005 |
| WO | WO 2005/098982 | 10/2005 |

OTHER PUBLICATIONS

Candle Impressions® Website (Formerly Candles of Paradise) at http://www.candleim pressions.net/cgi-ole/cs.waframe.homepage dated Nov. 14, 2005 (1 page).
Webpage http://www.candleimpressions.net/cgi-cs/cs.waframe.menu?lang=1&topic=19189&click=... dated Nov. 14, 2005 (1 page).
Webpage http://www.candleimpressions.net/cgi-cs/cs.waframe.submenu?topic-19189&img_num=... dated Nov. 14, 2005 (1 page).
"Welcome to our Candles of Paradise Web Site," at http://www.candleimpressions.net/cgi-cs/cs.waframe.content?topic=19189img_num=&... dated Nov. 14, 2005 (1 page).
"Battery Operated Flickering Wax Candles," at http://www.candleimpresisons.net/cgi-cs/cs.waframe.content?topic=19538 &lang=1 dated Nov. 14, 2005 (3 pages).
"Battery Operated Flickering Wax Candles with Candle Holders," at http://www.candleimpressions.net/cgi-cs/cs.waframe.conent-?topic=26227&lang=1 dated Nov. 14, 2005 (3 pages).
"Battery Operated Wall Sconces with Flameless Wax Candles," at http://www.candleimpressions.net/cgi-cs/cs.waframe.content-?topic=26221&lang=1 dated Nov. 14, 2005 (2 pages).
"Battery Operated Flickering Candle Light Fixtures," at http://www.candleimpressions.net/cgi-cs/cs.waframe.content?topic=19541 &lang=1 dated Nov. 14, 2005 (5 pages).
"Solar Operated Flickering Candle Light Fixtures," at http://www.candleimpressions.net/cgi-cs/cs.waframe.content?topic=19542 &lang=1 dated Nov. 14, 2005 (1 page).
"Candle Fire Safety," at http://www.candleimpressions.net/cgi-cs/cs.waframe.content?topic=19530&img_num=2 dated Nov. 14, 2005 (1 page).
Web Page http://www.nam.lighting.philips.com/us/led/ dated Oct. 21, 2005 (1 page).
Web Page http://www.nam.lighting.philips.com/us/led/features_specs.php?mode=1 dated Oct. 21, 2005 (2 pages).
Web Page http://www.nam.lighting.philips.com/us/led/features_specs.php?mode=2 dated Oct. 21, 2005 (2 pages).
Web Page http://www.amazon.com/exec/obidos/tg/detail-/B0009WRJ58/103-3573233-1695062?v=glance&s=home-...dated Oct. 21, 2005 (3 pages).
Web Page http://www.amazon.com/exec/obidos/tg/detail/-/B0009WRJ58/103-3573233-1695062?v=glance&s=home-...dated Oct. 21, 2005 (3 pages).
Photographs of "Everlasting Tealights" packaging and device—Made in China, designed and imported by the Gerson Company—Olathe, KS, (5 pages).
International Search Report and Written Opinion in PCT/US2006/042971 dated Mar. 22, 2007.
International Search Report and Written Opinion in PCT/US2006/042919 dated Apr. 20, 2007.
Office Action in U.S. Appl. No. 11/140,329 dated Apr. 27, 2007.
Office Action in U.S. Appl. No. 11/050,242 dated Jul. 19, 2007.
International Search Report and Written Opinion in PCT/US2007/025160 dated Apr. 11, 2008.
Office Action in U.S. Appl. No. 11/050,169 dated Oct. 15, 2008.
Office Action in U.S. Appl. No. 11/264,952 dated Oct. 24, 2008.

* cited by examiner

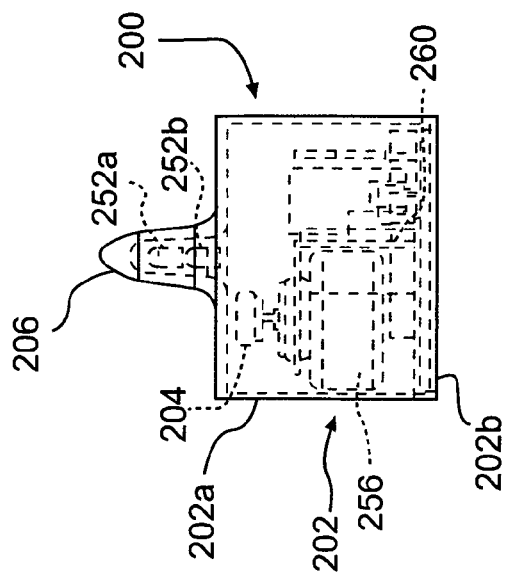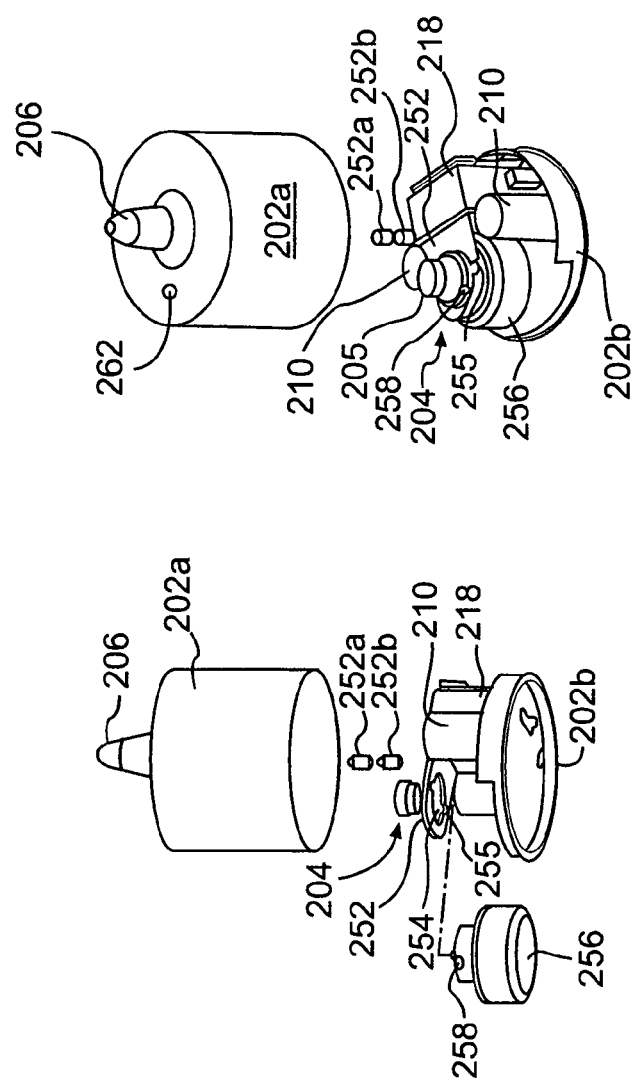
FIG. 7A  FIG. 7B  FIG. 7C

DEVICE PROVIDING COORDINATED EMISSION OF LIGHT AND VOLATILE ACTIVE

RELATED APPLICATION

This application claims the benefit of U.S. Provisional Application No. 60/541,067, filed Feb. 3, 2004.

BACKGROUND OF THE INVENTION

1. Field of the Invention

Our invention relates to the integrated presentation of ambient conditions. More specifically, our invention relates to the controlled and coordinated emission of light and volatile active, e.g., a fragrance, into a given area from a single device.

2. Description of the Related Art

Because of their wide array of shapes and sizes, as well as the seemingly limitless number of available scents, few things are quite as versatile at setting the ambience in an area as scented candles. Scented candles are not without drawbacks, however. For example, dripping wax can damage furniture and the skin and, in the extreme, an open flame can lead to a structure fire.

To account for the common problems associated with candles, electronic lighting devices that have a flickering candle appearance, such as those disclosed in U.S. Pat. Nos. 5,013,972 and 6,066,924, are generally known in the art. In the '972 patent, two side-by-side lamps are alternatingly turned on and off at such frequencies that a flickering is perceived. Similarly, the '924 patent discloses circuitry used to control two light bulbs in close proximity to each other such that the bulbs flicker. Moreover, the circuitry and bulbs of the '924 patent are contained within a container of a size and shape similar to common flat candles. While these patents may suggest devices that mimic the visual aesthetics of a candle, they fail to provide the scented candle experience, i.e., they fail to emit fragrance in addition to light.

Fragrance dispensers are also generally known. For example, it is known to emit fragrance from an aerosol container upon the activation of a trigger by a user. Also, other methods utilize the evaporative properties of liquids, or other vaporizable materials, to cause vapors with desired properties to be distributed into the ambient air. For example, U.S. Pat. No. 4,413,779 discloses a glass container containing a fluid into which two rigid porous nylon wicks extend. The wicks contact a rigid plastic porous element. In use, the wicks transport the fluid from the glass container to the ambient air. As a further example of air fresheners, the art is also generally aware of atomizer assemblies for releasing fragrance from a wick that draws fragrant liquid from a reservoir. For example, commonly assigned U.S. Pat. No. 6,296,196 and commonly assigned and copending U.S. patent application Ser. No. 10/412,911, filed Apr. 14, 2003, both discussed in detail below, disclose such assemblies. The '196 patent and the '911 application are hereby incorporated by reference. Although these representative devices provide fragrance emission, they do not provide the visual aesthetic of a candle.

SUMMARY OF THE INVENTION

Our invention provides a device that emits both light and scent (or other active ingredient) similar to a scented candle. More particularly, our invention is directed to an improved candle that employs a unique design combining a flameless flickering effect and an effective, reliable volatile active delivery system.

More specifically, in an aspect of our invention, a flameless candle that releases a volatile active includes at least one LED, a cartridge mount, and a support structure. The at least one LED emits a flickering light that emulates a flame of a candle. The cartridge mount receives and secures a replaceable cartridge containing a volatile active to be released into the atmosphere over time. The support structure supports the at least one LED and the cartridge mount. The support structure is configured to allow airflow across the replaceable cartridge when the replaceable cartridge is mounted in the cartridge mount.

According to another aspect of our invention, a flameless candle includes at least one LED, a receptacle, control circuitry, and a housing. The at least one LED emits a flickering light that emulates a flame of a candle. The receptacle receives one or more batteries that provide power to the at least one LED. The control circuitry includes at least one of a current source controller that controls a current supplied to the at least one LED and a charge pump that supplies a predetermined forward voltage to the at least one LED when the voltage provided by the one or more batteries falls below a predetermined minimum voltage. The housing diffuses the flickering light emitted by the at least one LED. The at least one LED, the receptacle, and the control circuitry are disposed within said housing.

According to a further embodiment of our invention, a flameless candle for releasing a volatile active includes at least one LED, a housing, and a mount. The at least one LED emits a flickering light that emulates a flame of a candle. The housing includes a light diffusing portion. The at least one LED is mounted in the housing such that the light emitted therefrom is diffused by the light diffusing portion. The mount is disposed within housing, and mounts a replaceable cartridge containing a volatile active. The housing contains a first aperture that allows air to enter the housing and flow across the replaceable cartridge when the replaceable cartridge is mounted on the mount, and a second aperture that allows the air flowing across the replaceable cartridge when the replaceable cartridge is mounted on the mount to exit the housing.

A better understanding of these and other aspects, features, and advantages of the invention may be had by reference to the drawings and to the accompanying description, in which preferred embodiments of the invention are illustrated and described.

BRIEF DESCRIPTION OF THE DRAWINGS

FIGS. 7A-7C are views of a light and fragrance emitting device according to a further embodiment of our invention.

Throughout the figures, like or corresponding reference numerals have been used for like or corresponding parts.

DETAILED DESCRIPTION OF THE PREFERRED EMBODIMENTS

Figure 1:
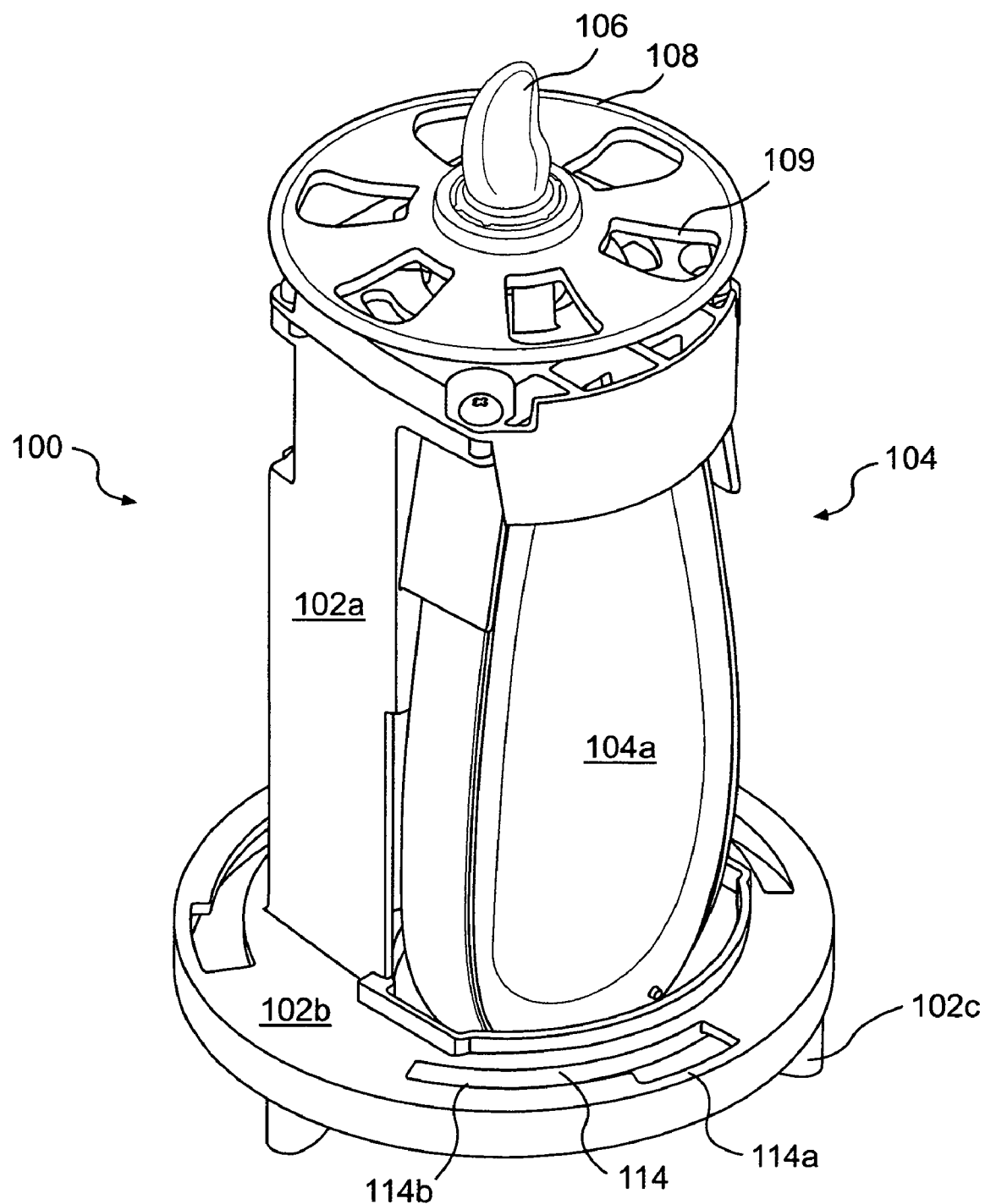
FIG. 1 is a perspective view of a light and fragrance emitting device according to an embodiment of our invention.

Our invention provides a device that emits both light and fragrance. Preferably, our invention provides a single device that mimics both the visual and olfactory aesthetics of a scented candle, without an open flame and with an improved fragrance delivery system.

While a preferred embodiment of our invention includes emission of a fragrance, and much of the discussion below will be with regard to emission of a fragrance, we also contemplate that the dispenser of our invention may alternatively dispense other volatile actives. Such alternate volatile actives may include, for example, disinfectants, sanitizers, insecticides, insect repellants, medicaments, and such other active ingredients that are usefully dispersed into the air. As will be recognized by one of ordinary skill in the art, other volatile actives may also be introduced to the ambient environment via dispensers in much the same way as fragrances.

As generally seen in the figures, preferred embodiments of our invention include a device for emitting light and fragrance. The device preferably includes an electrically-powered light source, a fragrance emitter, a power source, control circuitry, and a support structure. All of these components work together to provide a fragrant aroma and the appearance of a flickering flame, the flickering effect being provided by the electrically-powered light source.

Light Source

The light source of our invention is an electrically-powered light emitting device. While the light source may comprise any number of conventional lighting devices (including, for example, incandescent, halogen, fluorescent, etc.), in preferred arrangements, the light source comprises one or more light emitting diodes (LEDs). Particularly, as shown in FIGS. 7A-7C, the light source preferably includes two LEDs 252a, 252b.

An LED emits light of a dominant wavelength, or a very narrow range of wavelengths. (For purposes of simplicity, although we will refer to the dominant wavelength of the LED, that term should be interpreted to include a narrow range of wavelengths.) For instance, a blue LED will emit a dominant wavelength of light in the blue range of the color spectrum. This dominant wavelength is not substantially controllable for a given LED (although the dominant wavelength and intensity can drift slightly with temperature fluctuations, for instance). The intensity of the light, however, can be controlled for a given LED. For instance, LEDs can be controlled by altering the applied current so as to vary the intensity of the light of the LED's dominant wavelength. This can be achieved by a number of means; however, pulse width modulation (PWM) is preferred. Preferably, a controller receives instructions from a memory or an outside source regarding the operation of the LEDs. With PWM, the controller sets a duty cycle for each of the LEDs, thus defining the ON times and the OFF times of the LED. During the ON times, i.e., during the pulse width, a current is supplied to the LED, and the LED emits light. Accordingly, altering the pulse width will alter the amount of time that the LED emits light. Thus, the diode flickers on and off as the duty cycle is repeated over time. When this repetition is accomplished at a relatively high frequency, the on and off of the diode is imperceptible to an observer. Thus, the light will be perceived by the observer to be constantly emitted. When such is the case, a flicker effect can be achieved by altering the duty cycles over time to increase and decrease the intensity of the emitted light. Alternatively, the flicker effect can be achieved when the frequency of the duty cycles is relatively lower, in which case the on and off times of the diode are perceptible to the observer, thus providing the flicker. Of course, combinations of these flicker methods are also possible. Thus, greater control can be achieved than in conventional lights which cannot be turned on and off as rapidly due to the time it takes to reach full intensity (e.g., heat the filament in an incandescent bulb) and cease light emission (e.g., wait until the filament cools). (It would be recognized by one of ordinary skill in the art that, when using pulse width modulation to control one or more LEDs, substantially constant intensity lights and flickering lights may both be flickering at a high frequency imperceptible to an observer. Thus, flickering and constant intensity light should be understood herein to refer to perceived effects.)

Instead of altering the duty cycles, the controller may alternatively otherwise adjust how the current is supplied, thus altering the light emission properties of the LEDs. For example, methods utilizing an analog sine wave or a digital potentiometer are generally known in the art.

Consequently, in LED lighting, an observer will observe a color corresponding to the dominant wavelength for the LED, and the variation in the pulse width will have a dimming effect. This method of controlling LEDs is known in the art, and thus will not be discussed in more detail. Other methods of operating LEDs are also known, and the use thereof would be obvious to one of ordinary skill in the art.

When two LEDs are used, as in FIGS. 7A-7C, the two LEDs 252a, 252b are preferably arranged one above the other, i.e., the LED 252a is on a side of the LED 252b opposite to a base of the light and fragrance emitting device 200. Preferably, the upper LED 252a is controlled to emit light at a perceivable intermittence and/or varying intensity. For example, the pulse width of the LED may be adjusted over time to vary the perceived intensity or to provide perceivable intermittent on and off times for the LED. Thus, the flicker may be obtained by providing a constant (perceived) light emission of varying intensity, by providing an (perceived) intermittent light emission, or a combination of the two. In contrast to the upper LED 252a, the lower LED 252b is controlled such that light is perceived to be emitted substantially continuously and/or of a substantially constant intensity. This "continuous" light may be the result of a constant current being supplied to the LED or by providing a substantially constant pulse width over time, which gives the observer the perception of constant light when that LED is viewed on its own. Alternatively, the pulse width may be adjusted slightly over time to provide subtle intensity variations.

In this fashion, the LEDs 252a, 252b work to create a flicker effect. For example, when a conventional candle is lit, the base of the flame appears substantially steady, while the portion of the flame further from the base of the wick flickers more apparently. The present arrangement of the LEDs 252a, 252b mimics this visual characteristic. It is preferred that LEDs having a yellowish or amber hue be used. Specifically, it is preferred that the LEDs used have a wavelength of emission in the range of from approximately 580 nanometers to approximately 600 nanometers, and it is even more preferred that the LEDs used have a wavelength of emission in the range of from approximately 585 nanometers to approximately 595 nanometers.

Of course, we anticipate modifications to the light source of our preferred embodiment. For example, a single LED may be used that is controlled to have a varying intensity and/or perceivable intermittence, thereby providing a flickering effect. A device using a single LED results in a lower cost apparatus that consumes less power. Alternatively, more than two LEDs can be used, perhaps, to create the perception of a larger flame. Also, LEDs of many colors are known and could be used, for example, to more closely resemble a flame by using hues that are reddish, orangish, and/or yellowish. The colors can also be made to change, for example, using RGB LEDs (i.e., an array of red, green, blue LEDs). By so varying the types of LEDs used, as well as their arrangement, numerous aesthetics can be obtained, including varied colored shows, colored flames, and colored flickers. And, by adjusting the duty cycles of the LEDs, the brightness of the light may also be reduced or intensified, as dictated by design preference.

Moreover, when multiple LEDs are used, it is not required that one LED provide a light emission of substantially constant intensity while the other LED 252a provides a flicker effect. One or both may be held at a substantially constant intensity and one or both may emit flickering light.

Fragrance Emitter

A fragrance emitter is preferably provided integrally with our invention. The fragrance emitter preferably includes a replaceable container, having a fragrance in any one of a number of conventional forms, including gel and liquid forms. In such gel and liquid forms, the fragrance is generally incorporated with a carrier substance, for example, by impregnation, intermixture, coating, solubilization, or other means. The fragrance and carrier are then contained in a container, for example, a cartridge, a pouch, a bladder, a reservoir, or the like, and a portion of the container is formed such that the fragrance can permeate therethrough. For example, the fragrance may be emanated through the permeable portion when air passes thereover, or the fragrance may be vaporized by the application of heat and emanated from the container. In such a case, the dispenser may have a controllable heating device to vary the rate at which the volatile is released from the container or a mechanical controller for controlling the airflow around the fragrance to be vaporized (such as a shield or fan).

Another type of fragrance emitter is a wick-based emanator, in which a fragrant liquid is drawn from a container, such as a reservoir, by a wick, via capillary action, and dispersed into the atmosphere. Additionally, the fragrance dispenser may use an atomizer to emanate the fragrance from the wick.

Specifically, this atomizer-type fragrance dispenser uses a wick to draw a fragrant liquid from a reservoir. An orifice plate, having minute tapered orifices therethrough is disposed in contact with the wick. Connected to the orifice plate is preferably an actuator element made of, for example, a piezoelectric ceramic material. The actuator element is preferably annularly shaped and the orifice plate is preferably circular. Electrical power, in the form of high frequency alternating voltages, is applied to the opposite upper and lower sides of the actuator element to produce electrical fields across the actuator element. These fields cause the actuator element to expand and contract in radial directions, causing the orifice plate to flex, such that a center region thereof vibrates up and down. As a result of this vibration, the liquid passes through the orifices of the orifice plate, and is ejected from the upper surface of the orifice plate in the form of small droplets.

A more detailed explanation of this sort of atomization device may be found in commonly assigned copending U.S. patent application Ser. No. 10/412,911, filed Apr. 14, 2003, which is discussed above. In addition, a more detailed explanation of a support structure for the atomizing device may be found in commonly assigned copending U.S. patent application Ser. No. 10/241,215, filed Nov. 26, 2002. The disclosure of the '215 application is also hereby incorporated by reference.

Of course, other fragrance emitting devices may be substituted as desired in consideration of design choices, manufacturing costs, etc. Moreover, even within each type of dispenser, variations are possible, as would be appreciated by one of ordinary skill in the art.

Power Source

The power source supplies power to light the light source, and if required, to the fragrance emitter to aid in release of fragrance. For example, the power supply will supply voltages to the upper and lower surfaces of the actuator plate in the atomization-type fragrance dispenser discussed above. Additionally, the power source may be used to power additional components, for example, a fan or a heater.

In a preferred embodiment, the power source comprises one or more batteries. When one battery is used, a voltage step-up or a charge pump (described in more detail below) may be used to ensure sufficient power to the components. The batteries may be replaceable, or they may be rechargeable. If rechargeable batteries are used, they may be removed for recharging, or an adapter may be provided on the device such that the batteries can be charged without being removed from the device. For instance, a receptacle may be incorporated into the device to receive a plug that supplies power from an electrical outlet.

It is not required, however, that the power source comprise batteries. For example, power for the device may be derived directly from an electrical outlet. As will be appreciated by one of ordinary skill, however, the use of alternate power sources may require that the device further include an AC to DC converter.

Control Circuitry

As used throughout, the term "control circuitry" is intended to be a representative term that encompasses all controls that can be used to embody our invention. For example, the preferred embodiments are discussed below with reference to microcontrollers and/or circuit boards, which all constitute control circuitry. Further contemplated examples of control circuitry that may be used to embody our invention are an Application Specific Integrated Circuit (ASIC), a microprocessor, and an arrangement of one or more resistors and/or capacitors. Control circuitry may or may not include software. These examples of control circuitry are not limiting, however. Other control circuitry may also be used.

The control circuitry is generally used to control the operation of the device and is powered by the batteries. Specifically, the control circuitry is designed to provide the signals for controlling the operation of the light source. When one or more LEDs are provided as the light source, the microcontroller may alter the duty cycles of the LEDs to control the perceived intensity of the emitted light, thereby creating the candle-like flicker effect.

When at least two LEDs are used, and one LED receives a constant current to emit light perceived to be substantially constant in intensity, that LED can be controlled separately from a circuit board, either to receive a power supply from the power source, when the device is turned on, or to not receive power, when the device is turned off. In other words, when one LED emits constant intensity light, it is not necessary to provide means for adjusting the pulse width within a duty cycle thereof (such as the microcontroller). In this case, the microcontroller may adjust the operation of only the LEDs that flicker. In other embodiments, the constant emission LED may be controlled by pulse width modulation set by the controller such that the frequency of the pulse width is imperceptible to an observer. In this manner, the intensity of the constant emission LED may be varied slightly to add to the overall flicker presentation.

Also, when a fragrance dispenser including an atomizer is used, the control circuitry may include circuits for converting power from the batteries to the high-frequency alternating voltages required to expand and to contract the actuator member, thereby emitting fragrance from the fragrance dispenser. In addition, the microcontroller may control a fan, a heating element, or the like, to aid in dispersion of the fragrance. Furthermore, the microcontroller may include controls for automatically turning on and or off one or both of the light source and the fragrance dispenser. For example, a timer may be included, and upon a predetermined elapsed time, some or all of the components will shut off.

The control circuitry may also serve other functions. For example, when batteries are used as the power source, it may be desirable to incorporate a charge pump. As is understood, LEDs require a forward voltage to operate. While this forward voltage may vary depending on, for example, the color of the light emitted by the LED, the preferred LEDs used with our invention may require anywhere from approximately 1.8 volts to approximately 2.5 volts as a forward voltage, but typically require in the range of from approximately 2.0 to approximately 2.1 volts. The charge pump ensures that a supply voltage to the LEDs exceeds the forward voltage of the LEDs, when the voltage supplied by the batteries lessens, over time, to a voltage below the forward voltage. The charge pump uses one or more capacitors to store power in order to generate a voltage level greater than that supplied by the battery. Thus, the charge pump can boost the voltage level to greater than the forward voltage. In this manner, the LEDs will continue to operate, even though the batteries are depleted to a point at which they are outputting a lower voltage. Consequently, a single set of batteries can power the device for a longer period of time than if no charge pump was used.

In addition, the control circuitry may incorporate a constant current source, which ensures that a constant current is applied to the LEDs, regardless of the battery voltage. Otherwise, a higher voltage and corresponding LED current would be supplied at the beginning of the battery's life, which would trail off as the battery is used. This would lead to an observer perceiving a brighter flicker when a new set of batteries is installed, and having that intensity wither as the battery output decreased to the forward voltage or below, at which point the charge pump would activate. Thus, by providing a constant current source, the LEDs can emit a light having a constant intensity over time, which prevents a noticeable dimming as the batteries begin to lose power. When a charge pump is used, however, current is not constantly supplied to the LEDs. Because there must be a time interval during which the charge pump charges, the power provided through the charge pump is by its nature intermittent. Therefore, a constant current is not supplied to the LEDs, and thus the constant current source would not function properly, when a charge pump is operating.

However, it is possible to supply a constant average current to the LEDs, via a constant average current source. In a constant average current source, a current is supplied during a portion of a cycle to achieve an average current over the cycle that would equate to the constant current that would otherwise be provided. Specifically, where a constant current source supplies a constant current to each of the two LEDs, a constant average current source supplies (i) a current (typically constant) to the first LED for a portion of a cycle (the cycle is set based on preferred design aspects and is not the same as the duty cycle referred to with respect to the light intensity modulation of the LEDs), (ii) a current (typically constant) to the second LED for another portion of the cycle, and no current to either LED during a final portion of the cycle. For instance, when two LEDs are provided, a constant current source would supply a constant current of, for example, 15 mA to the first LED and 15 mA to the second LED when the LEDs are enabled. However, for example, a constant average current source supplies 45 mA to the first LED for one-third of a cycle and 45 mA to the second LED for another one-third of the cycle, with no current being supplied during the final one-third of the cycle. Alternatively, because the voltage may slightly decline over the two-thirds of the cycle in which the LEDs are enabled, the LED enabled directly after charging may appear slightly more intense than the second LED enabled. Accordingly, an alternative cycle for driving the LEDs could consist of, in order, a first one-sixth in which neither LED is enabled, a second one-sixth in which the first LED is enabled, a third one-sixth in which the second LED is enabled, a fourth on-sixth in which neither LED is enabled, a fifth one-sixth in which the second LED is enabled, and a final one-sixth, in which the first LED is enabled. In this manner, the first LED is enabled directly after charging half of the time, and the second LED is enabled directly after charging the other half of the time. Thus, in both examples, the average current supplied to the LEDs is the same as that provided by the constant current source; however, in this manner, no current is provided to either LED during a portion of the cycle, thus reserving a time gap for the charge pump to operate. Consequently, when the charge pump is activated, there is no change in operation since the charge time is already a dedicated part of the cycle. As would be understood by one of ordinary skill, the cycle used by the average current source should be of a sufficiently high frequency that the LEDs will be perceived to be constantly emitting light (or to be emitting a perceived flicker, as discussed above).

Many combinations of one or more of the charge pump, the constant current source, and the constant average current source may be used. For example, a constant current source may be used until such time that the charge pump is activated, and thereafter a constant average current source may be used. For the sake of convenience, the term current source controller will be used herein to refer to a mechanism for providing a constant current or a constant average current. This may be achieved with a constant current source, a constant average current source, or a combination thereof.

The control circuitry may also include controls to shut the device down when the batteries get below a certain voltage. In this way, the device will not continue to draw power from batteries that are dying, thus lessening the risk that the batteries will leak battery acid. Additionally, the control circuitry may be designed, in conjunction with sensors and/or switches to allow only operation of the LEDs when a fragrance emitter is disposed in the device.

Support Structure

Our invention also includes a support structure, provided to support the light source, the fragrance emitter, the power source, and the control circuitry, or some combination thereof. The term "support structure" is intended to encompass any and all of a chassis, a housing, a holder, and a base, as those terms are used in the description of the preferred embodiments, as well as similar structures used to support or contain the features of our invention.

Preferred Embodiments

Having generally described the components of our invention above, discussion will now be made of preferred embodiments of a light and substance emitting device according to our invention. These preferred embodiments include various novel arrangements of the above-described components, as well as additional features.

A first embodiment of our invention will be described with reference to FIGS. 1-6.

According to this preferred embodiment, a chassis 102 is provided. As illustrated, the chassis 102 comprises a chassis base 102b, and a chassis column 102a formed on the chassis base 102b. The chassis base 102b and chassis column 102a may be formed integrally, or as separate, attachable pieces. The chassis 102 may also include additional components. For example, one or more feet 102c may depend from the chassis base 102b, the feet 102c being attachable to the chassis base 102b, or formed integrally therewith. Additionally, as shown in FIG. 1, one or more slotted apertures, or slots 114, are formed through the chassis base 102b. As illustrated, the slots 114 are preferably arced and comprise a wider portion 114a and a narrower portion 114b. The slots 114 will be described in more detail below.

A fragrance emitter 104, a light-emitting tip 106, a collar 108, two batteries 110, and controls 112 are preferably disposed on the chassis 102. The batteries 110 are preferably removably detachable from the chassis 102, so they may be replaced and/or recharged as necessary. The controls 112 preferably include a printed circuit board 116, a controller 118 (e.g., an ASIC, a microcontroller, or the like), and two switches 120, 122, which act in conjunction with power supplied from the batteries to operate the device.

In this embodiment, the fragrance emitter 104 is preferably a replaceable fragrance cartridge 104a that is removably securable to a cartridge mount disposed on the chassis 102. The fragrance cartridge 104a used in this embodiment is preferably a passive fragrance emitter. More specifically, the releasable fragrance is preferably contained within a gel or liquid and is emitted into the air over time. Accordingly, fragrance is emitted as a result of airflow over the cartridge 104a, and no power is needed to emit the fragrance into the air. As discussed above, however, a device such as a fan or heater may also be used in conjunction with our device to increase the rate at which fragrance is emitted.

Figure 2:
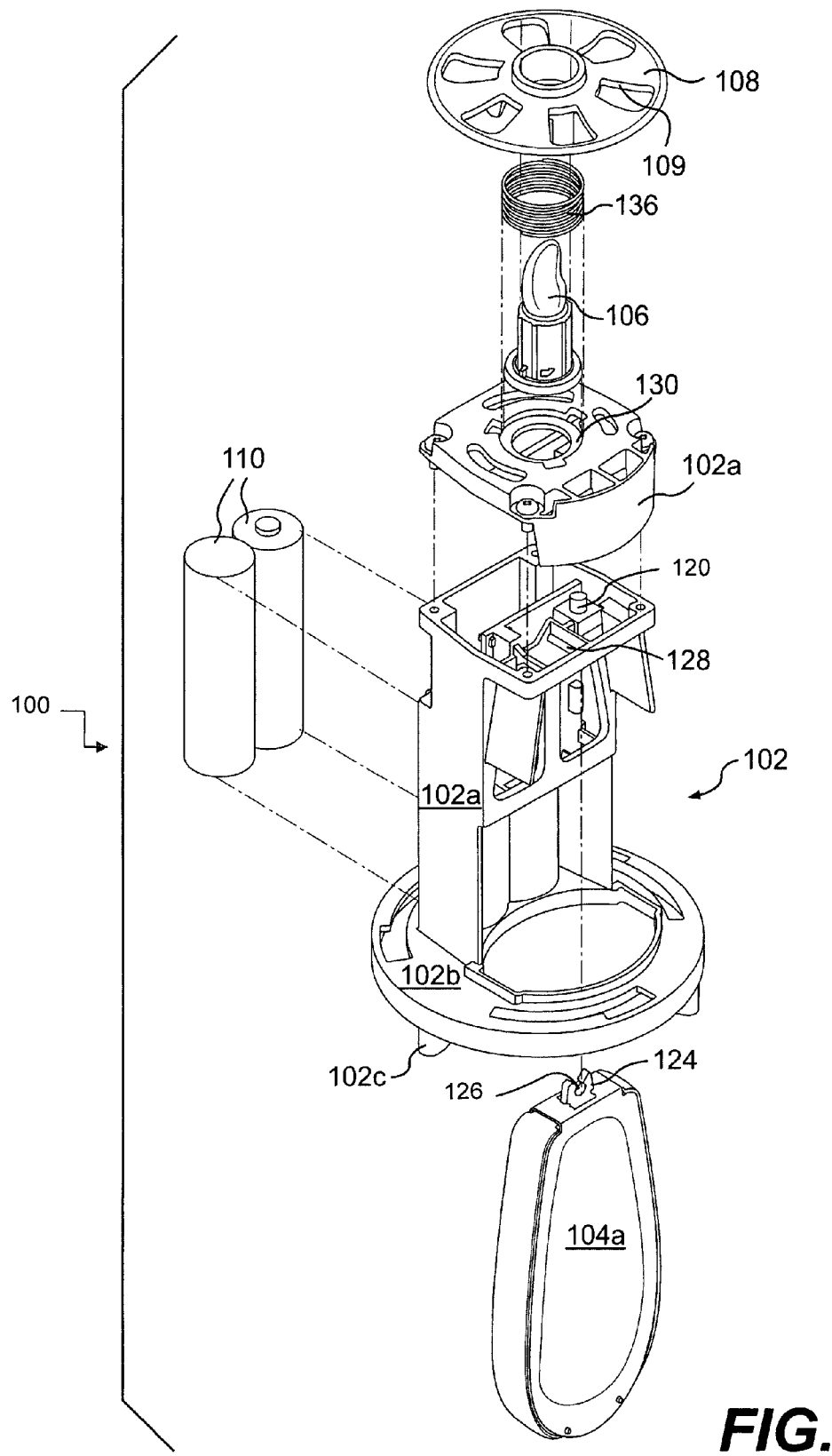
FIG. 2 is an exploded view of the device of FIG. 1.

In this embodiment, as shown in FIG. 2, the preferred cartridge 104a includes a protrusion 124, through which a substantially U-shaped opening 126 is formed, and the chassis column 102a has disposed thereon, or formed integrally therewith, a post 128, which serves as the cartridge mount. The opening 126 formed on the cartridge 104a and the post are designed such that the post fits within the opening, thereby attaching the fragrance cartridge 104a to the chassis 102. In this embodiment, the cartridge 104a is introduced and removed from the chassis 102 through an aperture formed through the base of chassis base 102b. (This opening also allows for airflow around the cartridge 104a to aid in release of the fragrance, as will be discussed in more detail below.) Thus, the opening on the cartridge 104a snappingly engages and disengages the post 128.

Of course, alternative methods are contemplated for securing/removing the fragrance cartridge 104a to/from the chassis 102. For example, the cartridge 104a may be attached and removed from a side of the chassis 102, in which case the U-shaped opening 126 may not be necessary. Instead, a circular opening may be sufficient to receive the post 128 therein. Additionally, the post and opening may not be provided at all. For example, the chassis 102 and cartridge 104a may be designed so an interference fit is formed therebetween to secure the cartridge 104a to the chassis 102. These examples are given only by way of example. Numerous cartridge mounts and cartridge configurations are contemplated, and would be known to one of ordinary skill in the art. Our invention contemplates any means by which a replaceable fragrance emitter can be removably attached to the chassis. Preferably, our invention will involve a mechanism for snappingly engaging and retaining the cartridge.

Figure 3:
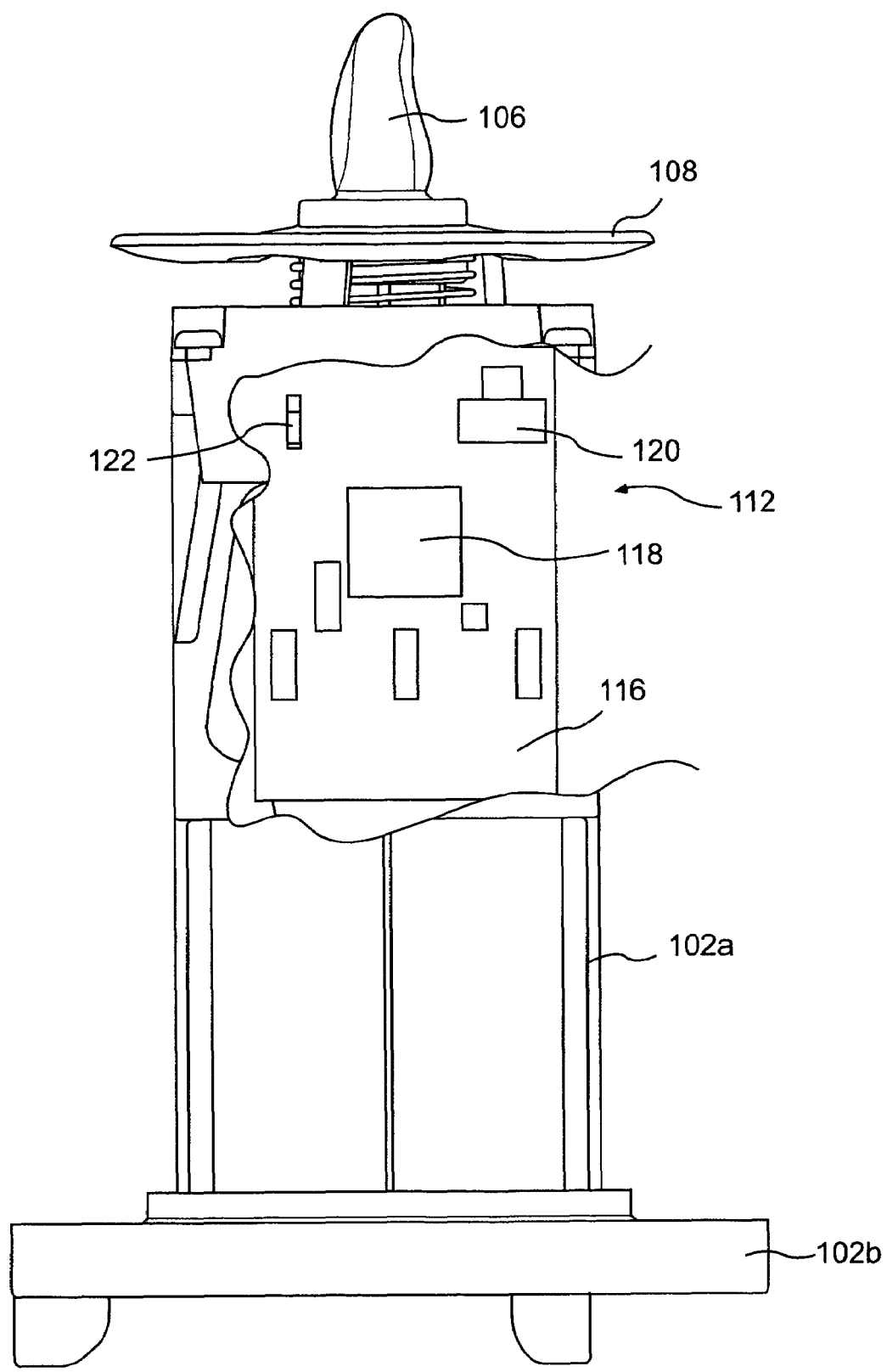
FIG. 3 is a side view of the device of FIG. 1 with the replaceable fragrance cartridge removed and a portion of the chassis cut away.

As a further feature of this embodiment, means are also provided for detecting the presence of the fragrance emitter 104. For example, the device may be controlled such that the LEDs will only emit light when a fragrance emitter 104 is attached. As shown in FIG. 3, a cartridge detector switch 122 is disposed on the chassis 102. For example, the cartridge detector switch 122 is actuatable between a normal position and an actuated position, and only when the cartridge detector switch 122 is in the actuated position will the LEDs emit light. Thus, in this embodiment, when the fragrance cartridge 104a is attached to the chassis 102, a portion of the cartridge 104a will contact, and thus actuate, the cartridge detector switch 122. This mechanical switch is provided only by way of example. One of ordinary skill in the art would recognize that other types of switches and/or sensors could similarly be used to detect the presence of the fragrance cartridge 104a.

The tip 106 is preferably disposed at the top of the chassis column 102a, and disposed therein is the light source. Preferably, two LEDs, as discussed above, are arranged one above the other within the tip 106. Light emitted from the LEDs is diffused by, and transmitted through, the tip 106. In this embodiment, as depicted in FIG. 2, the tip 106 is a separate component of the device, disposed within a bore 130 formed in the top of the chassis 102. The tip 106 may also be formed integrally with the chassis 102. By making the tip 106 a separate piece, however, the tip 106 may be replaceable, e.g., with other differently constructed, or colored, tips. Also, a separate tip 106 may be formed of a material other than that used for the chassis 102. Preferably, the tip 106 may be formed of one or more of plastic, glass, wax, and the like. Additionally, the tip 106 may be formed of a glow-in-the-dark material or of a material that continues to glow for a time after the LEDs are shut off.

Figure 6:
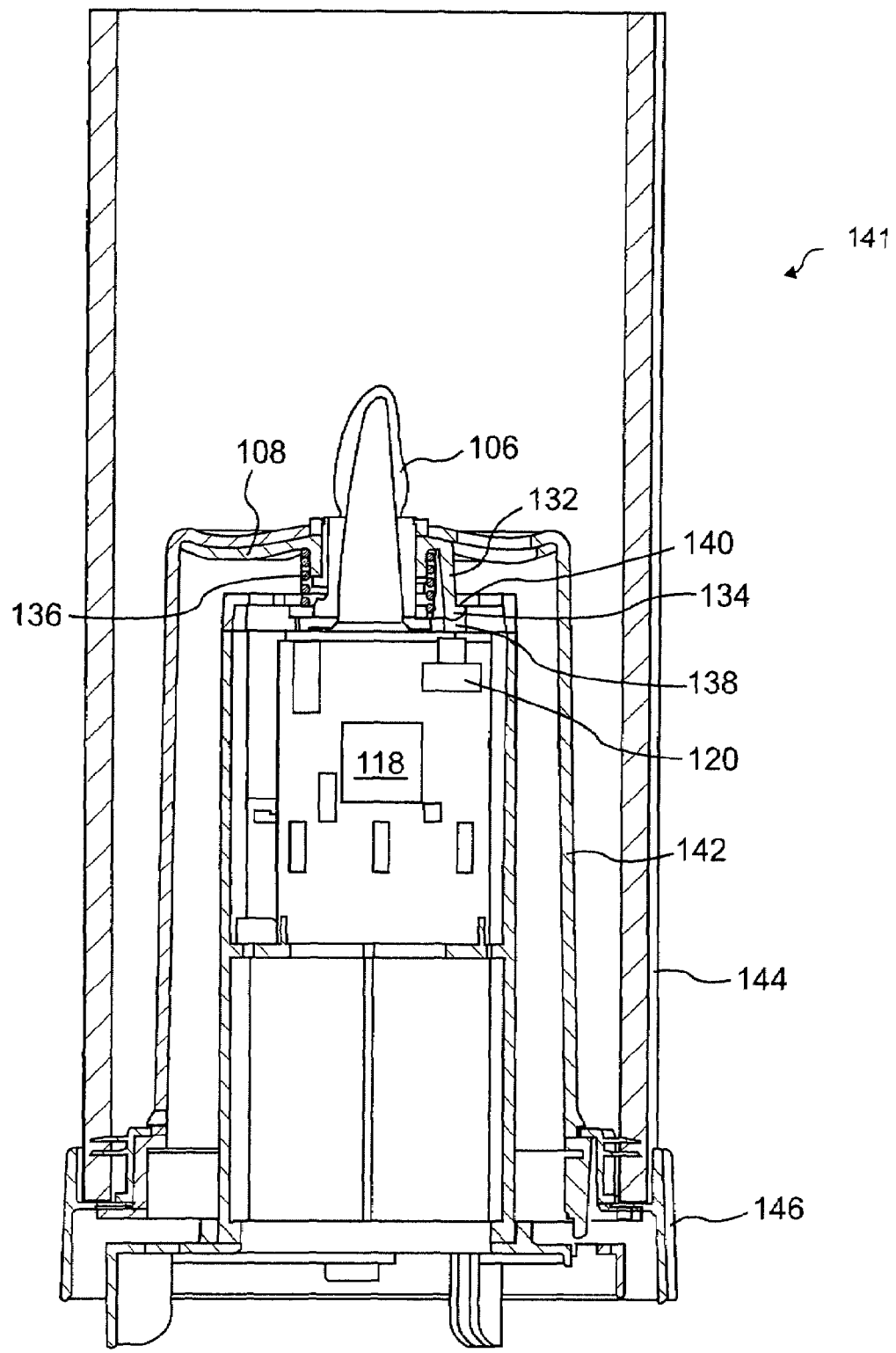
FIG. 6 is a sectional view of the device of FIG. 4, taken along section line 6-6 in FIG. 4.

In this embodiment, a collar 108 is also preferably disposed at the top of the chassis 102. The collar 108, while shown as a separate component, may also comprise a part of the chassis 102. The collar 108 has an aperture formed axially through the center thereof, and a portion of the tip 106 is preferably disposed within the aperture. The collar 108 is preferably actuatable with respect to the chassis 102. Preferably, a user actuates the collar 108 from a home position to turn the LEDs on and off. For example, as shown in FIG. 6, the collar 108 may have one or more tines 132 extending downwardly therefrom, and a lip 134 extends outwardly from a distal end of each of the tines 132. A spring 136 is disposed between the chassis 102 and the collar 108, to bias the collar 108 away from the chassis 102. As shown in FIG. 6, formed in the top of the chassis 102 is a plurality of tine-receiving bores 138 (one for each of the tines 132), each bore 138 having a shoulder 140. The tines 132 of the collar 108 are received within the bores 138, and the lip 134 of each of the tines 132 contacts the shoulder 140, to maintain attachment of the collar 108 to the chassis 102. Thus, when the collar 108 is actuated downwardly against the bias of the spring 136, the tines 132 slide downwardly within the bores 138. When pressure on the collar 108 is released, the bias of the spring 136 returns the collar 108 to the normal, or rest position. An on/off switch 120 is preferably disposed beneath one of the tines 132, such that actuation of the collar 108 causes the one of the tines 132 to actuate the on/off switch 120, controlling the LEDs to turn on and off.

Figure 4:
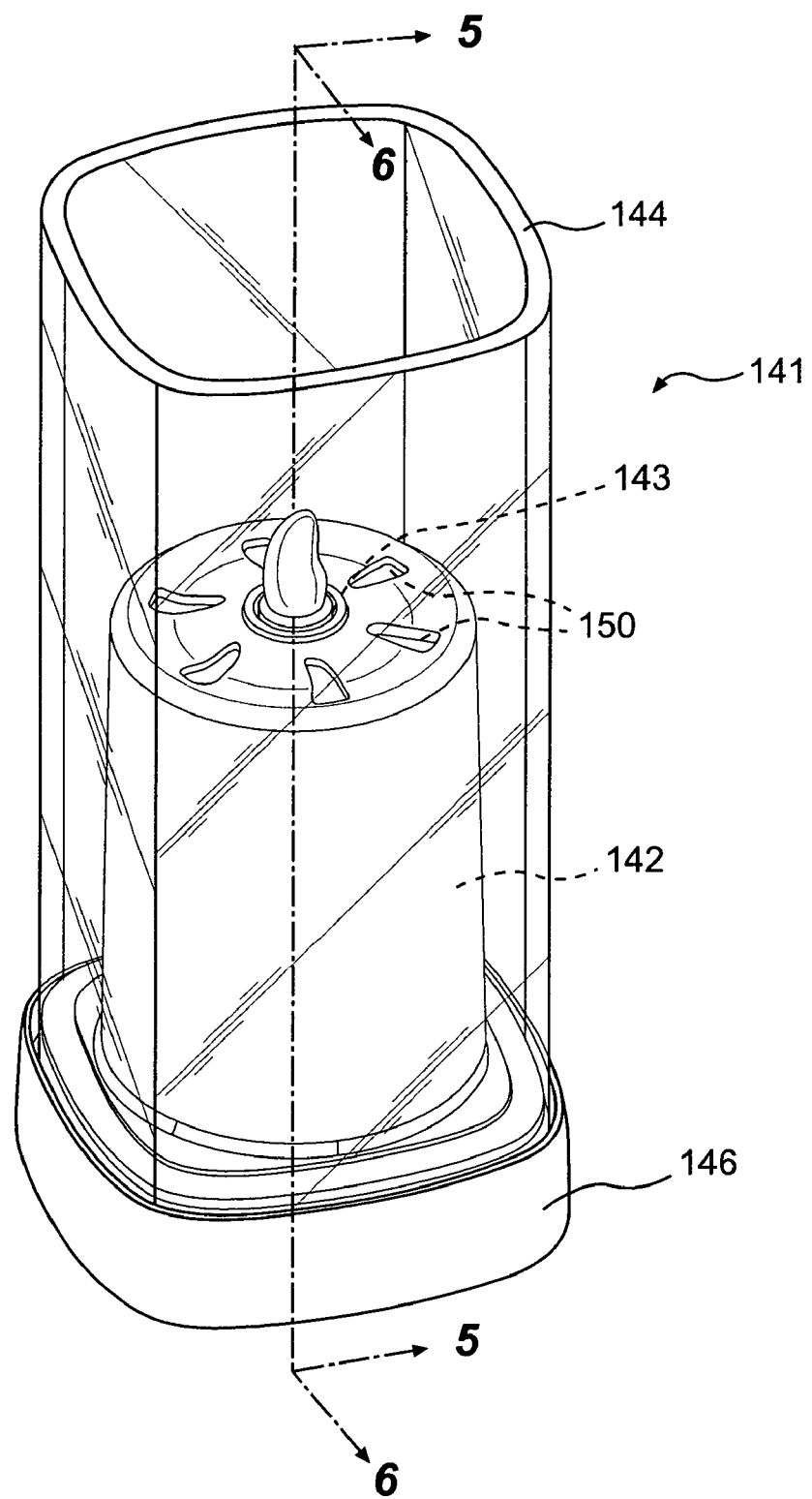
FIG. 4 is a perspective view of a light and fragrance emitting device according to an embodiment of our invention.
Figure 5:
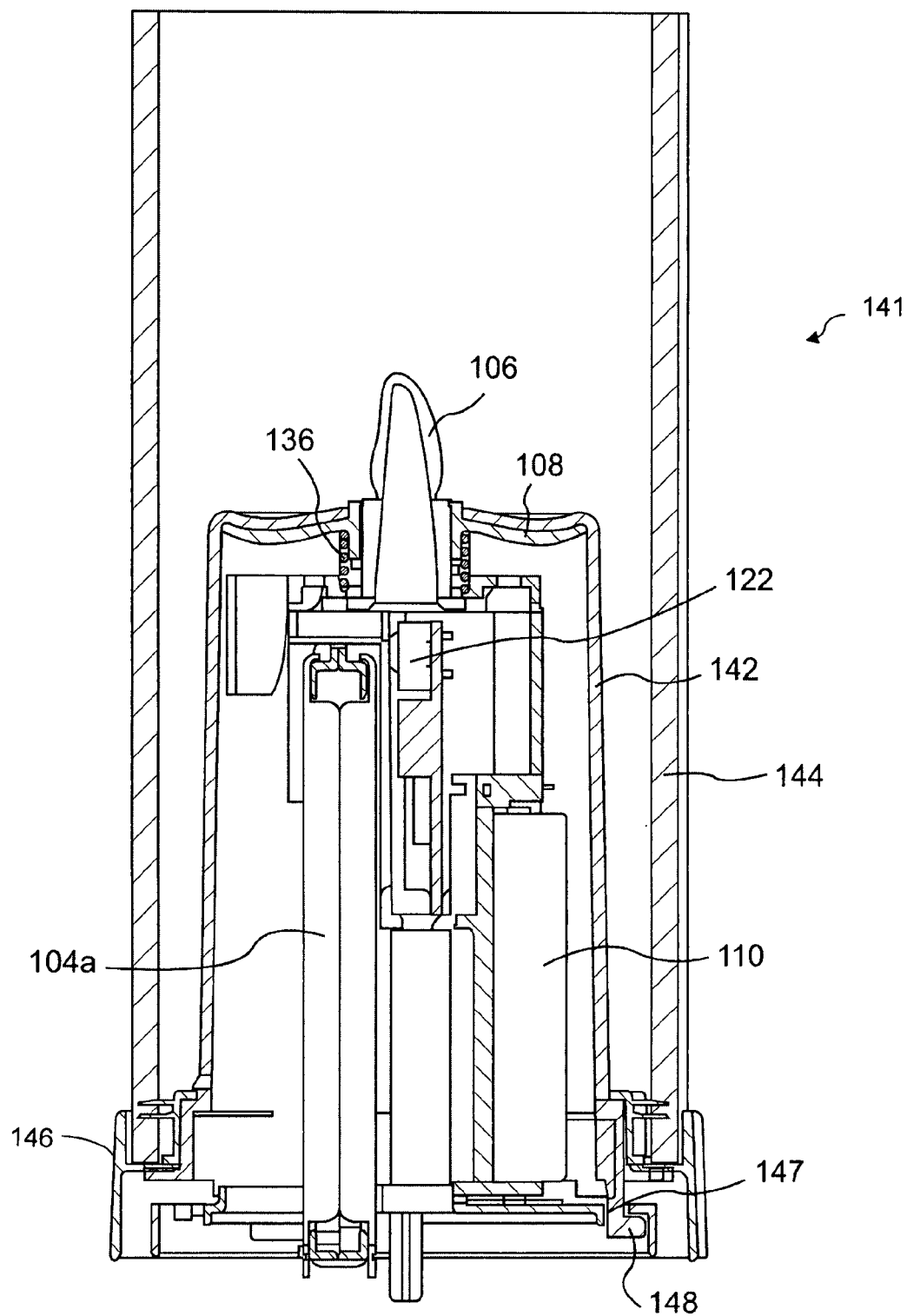
FIG. 5 is a sectional view of the device of FIG. 4, taken along section line 5-5 in FIG. 4.

The device shown in FIG. 1 and described to this point is a unitary device 100 that emits both a flickering light and a fragrance. While this device could be used as a stand-alone device, it is preferably used with a holder 141, as shown in FIGS. 4, 5, and 6.

The preferred holder 141 includes an inner shell 142 and an outer shell 144. The inner shell 142 is preferably generally cylindrical, with an open bottom and an aperture 143 formed centrally through a top thereof. When the holder 141 is lowered onto the unitary device 100, the tip 106 passes through the aperture 143, and an underside of the top of the inner shell 142 contacts the collar 108. In this manner, the holder 141 is rotatable with respect to the unitary device, i.e., the unitary device remains stationary while the inner shell 142 (and the remainder of the holder 141) rotate on the collar 108.

In addition, one or more protuberances 148 extend radially outwardly from extensions 147 depending downwardly from the open bottom end of the inner shell 142. The protuberances 148 are sized to pass through the wider portion 114a of the slots 114 formed in the chassis base 102b when the holder 141 is placed on the unitary device 100, but will not pass through the narrower portion 114b of the slots 114. The thickness of the extensions 147, however, is less than the width of both the wider portion 114a and the narrower portion 114b of the slots 114. Thus, the holder 141 is attachable and removable from the unitary device 100 only when the protuberances 148 are aligned with the wider portions 114a of the slots 114. But when the holder 141 is lowered completely onto the unitary device 100, the protuberances 148 are situated below the chassis base 102b, such that the extensions 147 are disposed in the slots 114. The holder 141 can thusly freely rotate with respect to the unitary device 100, with the rotation being constrained by the slots 114.

The outer shell 144 is preferably made of material through which the light emitted by the LEDs will pass. For example, the outer shell 144 may be made of glass, plastic, or wax. Additionally, the outer shell 144 may diffuse the light emitted by the LEDs. This diffusion may be in addition to the diffusion accomplished by the tip 106, or the tip 106 may not diffuse the emitted light (or may not be included), and only the outer shell 144 diffuses the light. The outer shell 144 may also be made of various colors, and may have formed thereon various colors, patterns, designs, and the like, depending upon the desired aesthetic.

The inner shell 142 and the outer shell 144 may be formed as a unitary holder 141, or they may be individual components that are assembled after manufacturing. Furthermore, the holder 141 may also include a base 146. The base may be purely decorative, or it may be used as a means for securing the inner shell 142 and the outer shell 144 together. As should be understood, when the holder 141 is situated on the unitary device 100, because the top of the inner shell 142 is in contact with the actuatable collar 108, downward actuation of the holder 141 will result in downward actuation of the collar 108, thus turning the LEDs on and off, as described above.

As can also be seen in the figures, when the holder 141 is placed on the unitary device 100, the inner shell 142 and the chassis base 102b define a substantially enclosed cavity in which the fragrance cartridge 104a, batteries 110, and controls 112 are disposed. The tip 106 extends upwardly from the substantially enclosed cavity, through the central aperture 143 in the inner shell 142. As described above, however, the preferred fragrance emitter 106 is a passive release system that requires airflow thereacross to release the fragrance into the air. Accordingly, it is necessary to allow for airflow through the cavity, across the fragrance cartridge 104a. In the preferred embodiment, this airflow is achieved through convection. In particular, apertures are formed through the top and bottom of the substantially enclosed cavity. As described above, an aperture through which the fragrance cartridge 104a is inserted and removed is formed through the chassis base 102b. Additionally, as shown in the figures, collar apertures 109 are formed through the collar 108 to allow passage of air, and venting apertures 150 are formed through the top of the inner shell 142. Thus, when a portion of the collar apertures 109 is aligned with a portion of the venting apertures 150, a passageway is formed through which air can flow between the ambient environment and the substantially enclosed inner cavity. In addition, as should be understood, rotating the holder 141 with respect to the unitary device, i.e., rotating the holder 141 within the slots 114, controls airflow through the collar apertures 109 and the venting apertures 150 by exposing more or less of the collar apertures 109 vis a vis the overlaying venting apertures 150. With this arrangement, ambient air preferably enters the device through the aperture formed through the chassis base 102b, and leaves through the collar apertures 109 and venting apertures 150.

A preferred light and fragrance-emitting device has now been described. Of course, modifications to this embodiment are contemplated. For example, providing differently patterned apertures, more or fewer apertures, and/or larger or smaller apertures can alter airflow through the device. For example, apertures may be provided through the sides of the inner shell 142 of the holder, in addition to, or instead of, the venting apertures 150 provided on the top of the inner shell 142. Also, the collar apertures and/or the venting apertures 150 may be made larger or smaller.

Additionally, while the collar 108 was described as being movable up and down with respect to the chassis 102 to turn the LEDs on and off, the collar 108 may alternatively be rotatable with respect to the chassis 102, to turn the LEDs on and off. Or, the collar 108 may not be actuatable at all, and switches may be provided on an exterior of the device to turn the LEDs on and off. Additional switches may also be provided to control lighting characteristics of the device. For example, switches may be provided to switch between different light shows, or different color LEDs.

A second embodiment of our invention will now be described with reference to FIGS. 7A-7C, 8, and 9. This embodiment includes features similar to those discussed above with respect to the first embodiment, and descriptions thereof will not be repeated. However, in this embodiment, the fragrance emitter preferably includes an atomizer, rather than a passive emanation system.

In this embodiment, a preferred light and substance emitting device 200 of our invention includes a chassis 202 comprising a chassis cover 202a and a chassis base 202b, which together form a cavity that encases each of two LEDs 252a, 252b, a fragrance emitter 204, two batteries 210, and a printed circuit board with microcontroller 218. The LEDs 252a, 252b are connected either directly or indirectly to both of the batteries 210 and the microcontroller 218. As discussed above, the fragrance emitter 204 of this embodiment preferably includes an atomizer assembly 205. The alignment of the fragrance emitter 204, the batteries 210, and the microcontroller 218 within the chassis 202 is not critical, but each of these components is preferably located below a top surface of the chassis cover 202a. Also, the LEDs 252a, 252b are preferably located substantially centrally with respect to a top surface of the device, and above the fragrance emitter 204, the batteries 210, and the microcontroller 218, i.e., on a side of the fragrance emitter 204, the batteries 210, and the microcontroller 218 opposite to the chassis base 202b. At least a portion of the LEDs 252a, 252b is preferably located above a top surface of the chassis cover 202a. By placing the LEDs 252a, 252b above the other components in this manner, the emission of light is not impeded by these components, so shadows are substantially prevented, and a more realistic-looking flame is created.

Although the alignment of the various features within the chassis 202 is not critical, the chassis 202 preferably includes a horizontal platform 252 (preferably disposed on the chassis base 202b) for aligning the fragrance emitter 204 within the chassis 202. The platform 252 preferably has a platform aperture 254 therethrough with one or more cutouts 255 formed on a periphery of the platform aperture 254. Preferably, a replaceable reservoir 256 for use in the fragrance emitter 204 comprises one or more nubs 258 (one corresponding to each of the cutouts 255 formed in the platform 252) formed on the reservoir 256. To insert the reservoir 256, a portion of the reservoir 256 is passed through the platform aperture 254 of the platform 252, with the nubs 258 passing through the cutouts 255. Once the nubs 258 clear the cutouts 255, the reservoir 256 is rotated such that the nubs 258 rest on the upper surface of the platform 252. Also, the top of the platform 252 supports the atomizer assembly 205 to which the reservoir mates.

Further, inner surfaces of the chassis 202 may contain various protrusions. These protrusions are preferably provided to aid in properly aligning various components within the chassis 202 and/or to protect components within the chassis 202. For example, a vertical protrusion 260 (shown in FIG. 7C) partitions an area for containing the fragrance emitter 204 from an area having the microcontroller 218. In this fashion, the microcontroller 218 is not accessible when the reservoir 256 is replaced, and, accordingly, inadvertent damage to, or accidental contamination of, the microcontroller 218 is averted.

The chassis cover 202a is designed such that it can be placed on the chassis base 202b, thus forming a unitary device 200. A protrusion or tip 206 is preferably disposed approximately centrally on the chassis cover 202a. The tip 206 extends generally axially, in a direction away from the chassis base 202b and forms a cavity in which the LEDs 252a, 252b are disposed when the chassis cover 202a is placed on the chassis base 202b. (As discussed above, the LEDs 252a, 252b are preferably arranged one on top of the other.) The tip 206 is substantially conical in shape and is preferably made of a material that diffuses the light emitted by the LEDs 252a, 252b. However, it may be desirable to alter the shape of the protrusion, when, for example, more than two LEDs are used, or the housing is relatively wide. For instance, the tip 206 may be more dome-shaped when a wider tip 206 is used with a wide device 200 (so as to keep the tip 206 relatively close to the chassis 202).

The tip 206 is preferably between approximately one-eighth of one inch (3.2 mm) and approximately three inches high (76.2 mm) and between approximately one-eighth of one inch (3.2 mm) and approximately three inches (76.2 mm) wide. The remainder of the device 200 is preferably between about two inches (50.8 mm) and about ten inches (254 mm) high and preferably between about one and one-half inches (38.1 mm) and about six inches wide (152.4 mm). Thus configured, the device 200 can substantially take on the size and shape of various conventional candles, while the tip 206, by encapsulating the LEDs 252a, 252b, simulates a flame.

The chassis cover 202a also includes an emission aperture 262 therethrough. When the chassis cover 202a is placed on the chassis base 202b, the emission aperture 262 aligns with the fragrance emitter 204. In particular, the emission aperture 262 is formed such that a fragrance dispensed by the fragrance emitter 204 passes through the chassis cover 202a to the ambient air, i.e., the chassis cover 202a does not impede the dissemination of the fragrance from the fragrance emitter 204.

The chassis cover 202a is preferably secured to the chassis base 202b, although such is not required. For example, as shown in FIG. 7A, the chassis cover 202a may be removably attached to the chassis base 202b such that access to, for example, the reservoir 256 and/or the batteries 210, may be gained for replacement purposes. When the chassis cover 202a is removably attachable to the chassis base 202b, a locking mechanism may be employed. For example, attractive magnets may be situated on the chassis cover 202a and the chassis base 202b, or the chassis cover 202a may include a feature that is designed for compatibility with a mating feature of the chassis base 202b. In this manner, only specific covers and bases can be used.

In another aspect, we contemplate that the chassis base 202b and the chassis cover 202a, when secured together to form the unitary device 200, may be relatively movable. Specifically, when the chassis cover 202a is cylindrical, it may be rotatable on the chassis base 202b. For example, the rotation of the chassis cover 202a may turn on and off the LEDs 252a, 252b and/or the fragrance emitter 204.

As an alternative to the removable chassis cover 202a, when, for example, a new scent is desired or the reservoir 256 is empty, the device 200 may include a hatchway for purposes of replacing the reservoir 256. Examples of two contemplated hatchways 264a, 264b are illustrated in FIGS. 8 and 9, respectively.

Figure 8:
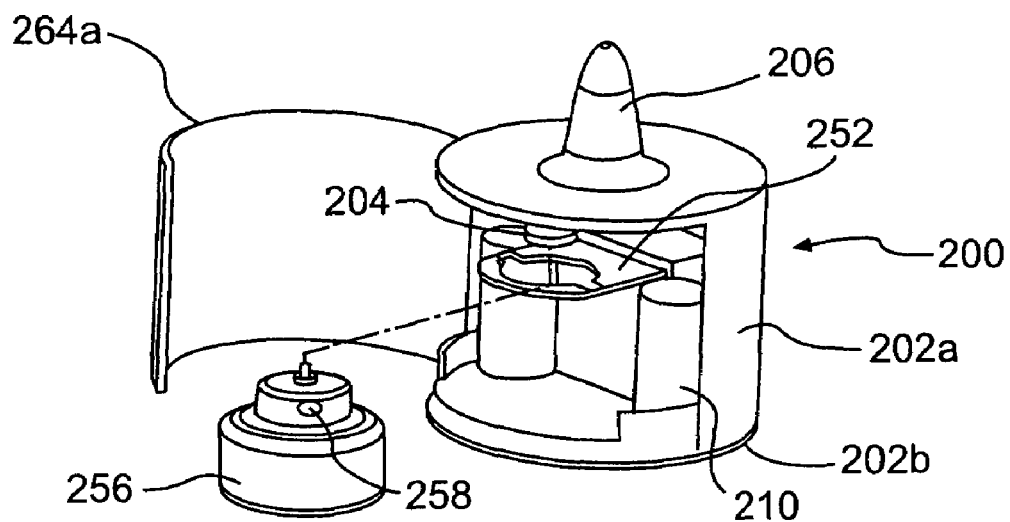
FIG. 8 is a perspective view of a light and fragrance emitting device according to another aspect of our invention.
Figure 9:
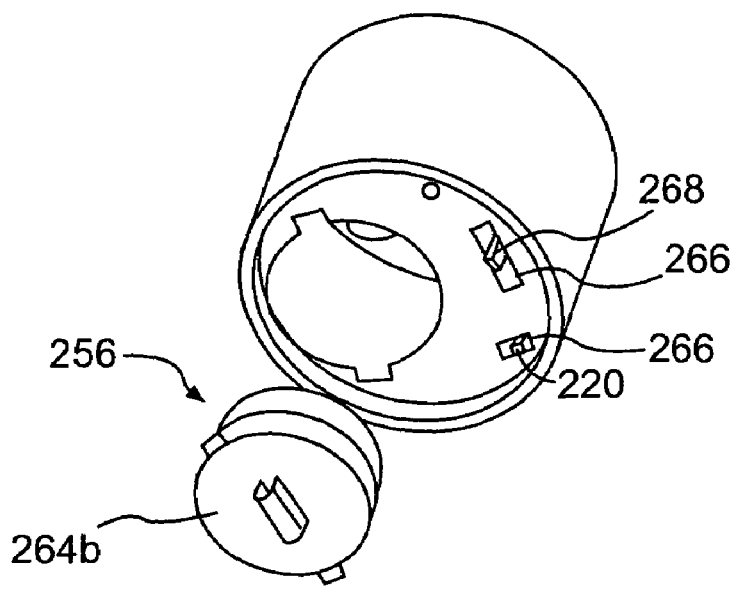
FIG. 9 is a perspective view of a light and fragrance emitting device according to still another aspect of our invention.
Figure 10C:
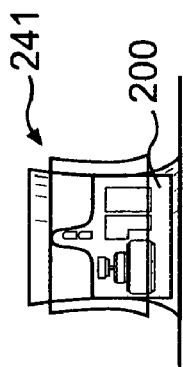
FIGS. 10A-10E illustrate further embodiments of a light and fragrance emitting device according to our invention.
Figure 10B:
Figure 10A:
Figure 10E:
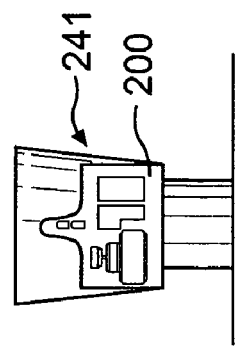
Figure 10D:
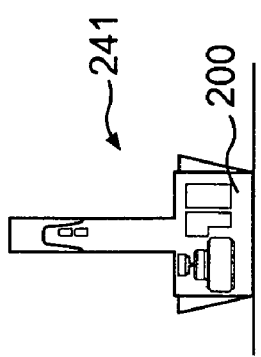

As shown in FIG. 8, the hatchway 264a may be located on the side of the device 200. The hatchway 264a is preferably hinged and is not completely removable from the device 200. As shown, the hatchway 264a may be opened to gain access to the reservoir 256. The hatchway 264a may also open to allow a user access to the batteries 210.

Alternatively, the hatchway 264b may be formed on the bottom of the device 200. For example, as shown in FIG. 9, a substantially circular hatchway 264b is removable from the device 200. In this configuration, the reservoir 256 is preferably coupled to the hatchway 264b. By coupling the reservoir 256 thereto, the hatchway 264b supports the reservoir 256, and, when assembled, ensures appropriate positioning of the reservoir 256 with respect to the atomizer assembly 205. Specifically, when the atomizer assembly 205 is used, removal of the hatchway 264b removes a portion of the reservoir 256 from contact with the atomizer assembly 205. The reservoir 256 is then removed from the hatchway 264b, a new reservoir 256 is coupled to the hatchway 264b, and the hatchway 264b is reattached, with the reservoir 256 properly aligning with the atomizer assembly 205. When the hatchway 264b of FIG. 9 is used, it may be unnecessary for the horizontal platform 252 to support and to align the reservoir 256, as the hatchway 264b will perform these functions. As such, the horizontal platform 252 will support the atomizer assembly 205, either directly, or preferably, with a support.

The chassis base 202b may also include one or more apertures 266 through which user control switches pass. A toggle switches 220, for example, allows a user to turn on and off one or more of the fragrance emitter 204 and the LEDs 252a, 252b, and a slider switch 268 allows a user to adjust the rate at which fragrance is emitted from the fragrance emitter 204. Alternatively or additionally, switches may also be provided that allow a user to adjust the light emission properties of the LEDs 252a, 252b, or to change an emitted light show.

Thus, like the first embodiment, the second embodiment provides a unitary light and substance emitting device 200 that may be used as a stand-alone device. The device 200 may be configured to mimic the size and shape of a conventional candle.

As should thus be apparent, in each of the preferred embodiments, a unitary device 100, 200 is provided that emits both a flickering light and a substance, such as a fragrance, to the ambient air. As discussed above, the preferred unitary device 100 of the first embodiment is preferably used in conjunction with a holder 141. The holder 141 is discussed in detail above, but is only an example. The unitary device 100 of the first embodiment may be used in conjunction with any number of holders. Similarly, the unitary device 200 of the second embodiment, much like typical replaceable candles would be placed into decorative holders, may be also be used in conjunction with unique holders. As used throughout this application, holder is meant to encompass any complete or partial encapsulation that holds, surrounds, is placed on, or otherwise encapsulates the unitary device.

Preferably, at least a portion of the holder used with the unitary device 100, 200 of either of the embodiments allows light to be emitted therethrough. FIGS. 10A-10E and 11A-11D show some representative alternative holder configurations that can be used in conjunction with a light and fragrance emitting device.

When a fragrance emitter is used, the emitted fragrance should also be emitted from the holder, and it is thus preferred that the holder provide ample ventilation. In particular, when an atomizer assembly is used, as in the second embodiment, the light and fragrance emitting device is preferably arranged in the holder such that the emission aperture through which the fragrance is dispensed is between about one inch (25.4 mm) and about six inches (152.4 mm) from the top of the holder, and substantially away from the inner surface of the holder. More preferably, the emission aperture is between about zero inches and about five inches (127.0 mm) from the top of the holder. With such an arrangement, buildup of fragrance on the inside of the holder is minimized. Moreover, the holder may be designed to aid the flow of the fragrance to the ambient environment. By tapering the holder such that the width of the holder narrows nearer the top of the holder, airflow will increase as it leaves the holder. Furthermore, we prefer that the holder not impede the emission of light from the LEDs. Specifically, the unitary device is preferably arranged in the holder such that the tip is between about one-half of one inch (12.7 mm) and about two inches (50.8 mm) from the holder. More preferably, the tip is between about one inch (25.4 mm) and about three inches (76.2 mm). The holder may also act as a diffuser. Furthermore, we envision that the holder could further include, for example, a fan for aiding in further dispersion of the fragrance emitted from the fragrance emitter.

The holder may comprise a single piece into which the device is placed. Alternatively, as shown in FIGS. 11A-11D, a holder 241 may also comprise a holder base 241a and a holder cover 241b. More specifically, the device is contained within, or alternatively comprises, the holder base 241a that receives and supports the holder cover 241b. The holder cover 241b, when supported by the holder base 241a, covers the tip 206. That is, light emitted from the housing by the respective illumination devices also passes through the holder cover 241b. Alternatively, the housing, e.g. the tip 206, may not diffuse emitted light, and only the holder cover 241b diffuses emitted light.

Figure 11B:
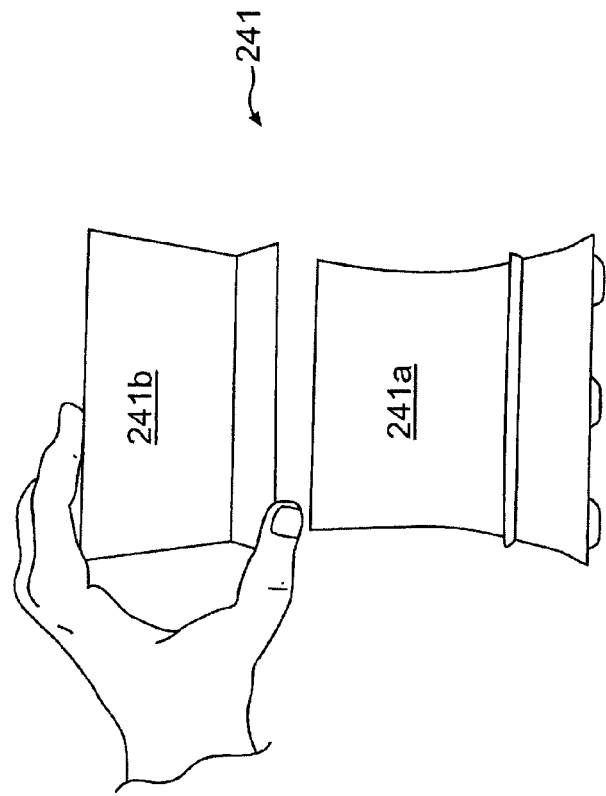
FIGS. 11A-11D illustrate configurations of holders to be used according to various aspects of our invention.
Figure 11A:
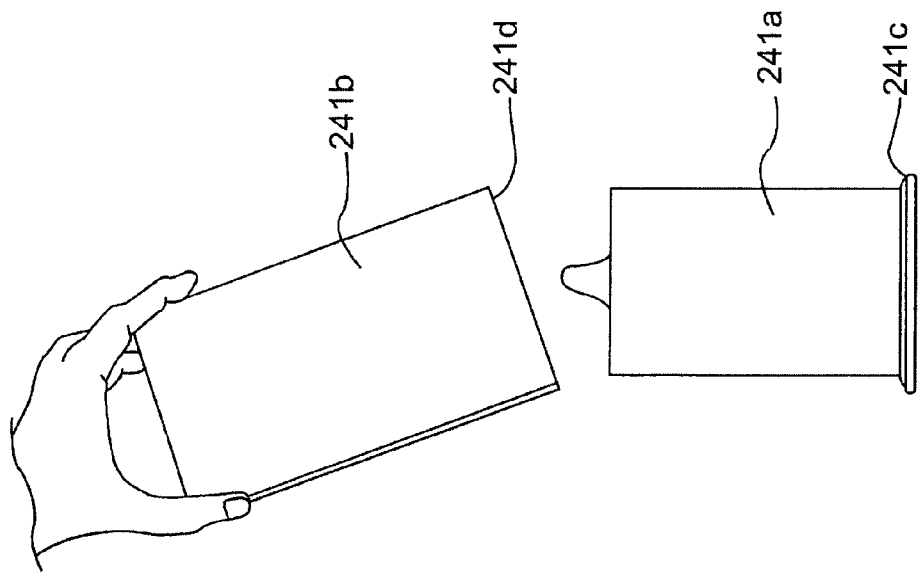
Figure 11D:
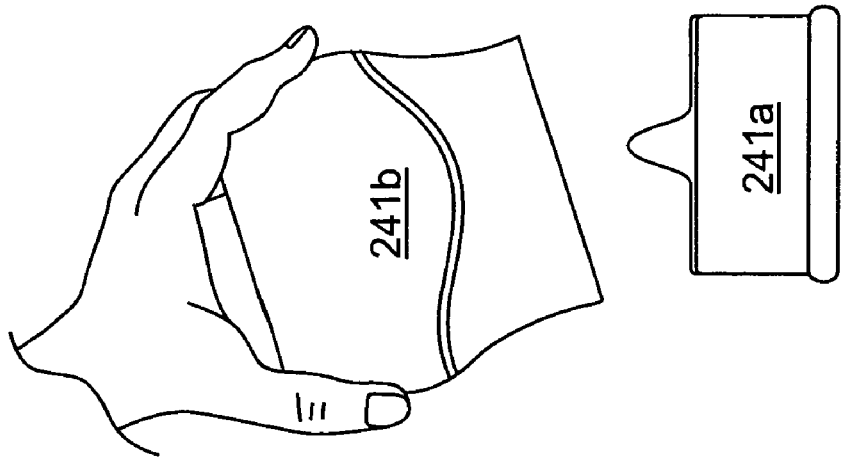
Figure 11C:
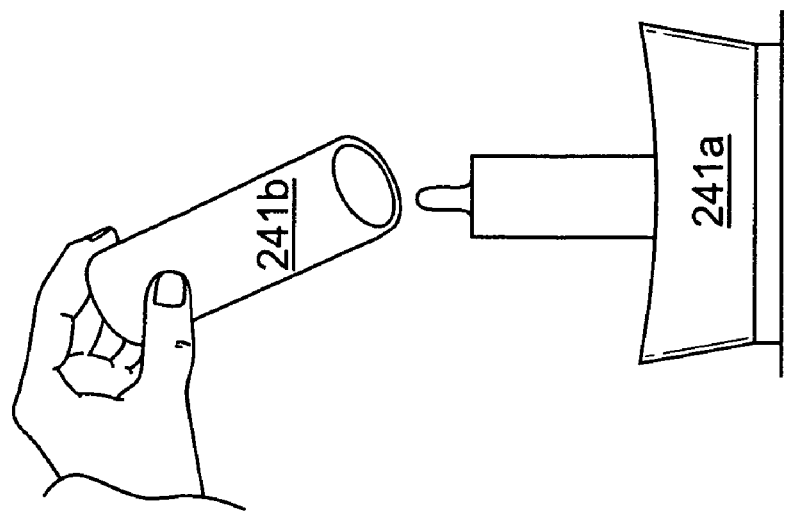

As a specific example of this embodiment, as shown in FIG. 11A, a holder base 241a containing a unitary device as described above in the preferred embodiments has a circumferential lip 241c extending radially outwardly from the holder base 241a. At least a lower portion 241d of the holder cover 241b is sized so as to engage the lip 241c of the holder base 241a, thereby resting the holder cover 241b on the holder base 241a. Other illustrative examples of holders 241 are shown in FIGS. 11B-11D.

While we envision that the holder cover 241b may rest on the holder base 241a, it is preferable that the holder cover 241b detachably attach to the holder base 241a. For example, the holder cover 241b may be designed to snap onto the holder base 241a. Alternatively, the holder cover 241b and the holder base 241a may be designed such that the holder cover 241b is rotated onto the holder base 241a, forming a locking engagement. In this or any configuration, the holder cover 241b may be relatively movable when secured to the holder base 241a. Specifically, when the holder cover 241b is generally cylindrical, it may be rotatable on the holder base 241a to turn the LEDs 252a, 252b and/or the fragrance emitter 204 on and off. Additionally, the engagement and disengagement of the holder cover 241b and the holder base 241a may act to turn the light source and/or substance emitter on and off. In this manner, the device would only operate with the holder cover 241b attached. Moreover, the holder cover 241b and holder base 241a may be specially designed such that only certain covers 241b can be used with the holder base 241a. For instance, the holder base 241a may include a reader (not shown) that reads an ID (e.g., an RF tag) of the holder cover 241b. In this manner, the device will not work unless the holder cover 241b has an appropriate ID.

When using the holder 241 according to this embodiment, we also envision that the holder cover 241b could emit a fragrance therefrom. For example, materials such as polyolefins are known that may be impregnated or infused with a fragrance. By forming the holder cover 241b of such a material, the holder cover 241b will emit a fragrance over time in addition to that emitted by the fragrance emitter 204. Alternatively, the device of this embodiment could not include the fragrance emitter 204, in which case, only the holder cover 241b will emit a fragrance. Also, with respect to the second embodiment described above, we note that the combination of chassis and base resembles a decorative candle, in which case a holder may not be desired. In such a case the base or chassis may be impregnated with a fragrance.

Because the holder cover 241b of this embodiment is removable, access to the device is facilitated (for example, to change the batteries) and the holder cover 241b can be easily replaced. For example, when the fragrance impregnated in the holder cover 241b is completely disseminated, a fresh, new holder cover 241b can easily be purchased and attached. Also, a user that has recently redecorated, or that wants to move the device to another room, may purchase a holder cover 241b having a certain color or other aesthetic feature. Moreover, replacement holder covers 241*b* may provide different smells. In other embodiments, the entire holder (or base) may be replaced.

While several preferred embodiments have been set forth above, many different embodiments may be constructed without departing from the spirit and scope of our invention. Our invention is not limited to the specific embodiments described above. To the contrary, our invention is intended to cover various modifications and equivalent arrangements included within the spirit and scope of our invention as defined by the claims. The claims are to be accorded the broadest scope, so as to encompass all such modifications, equivalent structures, and functions.

INDUSTRIAL APPLICABILITY

Our invention provides a device for light and/or fragrance emission. The device provides an overall desired aesthetic ambience in an area, such as a room.

We claim:

1. A flameless candle that releases a volatile active, said candle comprising:
    a plurality of LEDs that emit a flickering light that emulates a flame of a candle;
    a container mount;
    a support structure for supporting said plurality of LEDs so that said plurality of LEDs extends vertically from an uppermost surface of said support structure, said support structure also supporting said container mount; and
    a replaceable container including a volatile active to be released into the ambient environment over time;
    wherein said support structure is configured to allow air flow across the replaceable container;
    wherein the support structure comprises a chassis and a holder moveable with respect to the chassis, and wherein relative movement of the holder with respect to the chassis actuates a switch to control the plurality of LEDs.

2. The flameless candle according to claim 1, further comprising a power source disposed on said support structure for supplying power to said plurality of LEDs.

3. The flameless candle according to claim 2, wherein said plurality of LEDs are supported by said support structure so as to be positioned above the power source and said container mount.

4. The flameless candle according to claim 1, further comprising control circuitry disposed On said support structure for controlling said plurality of LEDs to emit the flickering light.

5. The flameless candle according to claim 4, further comprising a detector disposed on said support structure, wherein said detector detects the presence of the replaceable container when the replaceable container is mounted on said container mount, and wherein said control circuitry controls said plurality of LEDs to emit light only when said detector detects the presence of the replaceable container.

6. The flameless candle according to claim 1,
    wherein at least one aperture is formed through the chassis such that air may flow at least one of into and out of the chassis, the air flowing across the replaceable container when the replaceable container is attached to the support structure, and
    wherein relative movement of the holder with respect to the chassis covers and uncovers the at least one aperture, thereby adjusting an amount of air that flows trough the at least one aperture.

7. The flameless candle according to claim 1, wherein said plurality of LEDs comprises a first LED and a second LED arranged above the first LED, the first LED emitting light perceived by an observer to have a substantially constant intensity and the second LED emitting light perceived by the observer to be flickering.

8. The flameless candle according to claim 1, further comprising a fan disposed on said support structure, wherein the fan increases air flow across the replaceable container when the replaceable container is attached to the support structure.

9. The flameless candle according to claim 1, further comprising a heater mounted on said support structure, wherein said heater heats air that moves across the replaceable container, to aid in dispersion of the volatile agent from the replaceable container when the replaceable container is attached to the support structure.

10. The flameless candle according to claim 1, wherein the charge pump comprises one or more capacitors for storing voltage to ensure that the supply voltage to said plurality of LEDs exceeds the forward voltage of said plurality of LEDs, during the one portion of the cycle.

11. The flameless candle according to claim 1, further comprising an outer shell extending above a height of said plurality of LEDs.

12. The flameless candle according to claim 1, further comprising an outer shell from and containing said container mount and said plurality of LEDs.

13. The flameless candle according to claim 12, wherein the outer shell comprises a replaceable container detector switch, wherein attachment of the replaceable container to the support structure actuates the replaceable container detector switch to enable the plurality of LEDs to emit light.

14. The flameless candle according to claim 1, further comprising a replaceable container including a fragrance.

15. A flameless candle, comprising:
    a plurality of LEDs that emit a flickering light that emulates a flame of a candle;
    a receptacle that receives one or more batteries that provide power to said plurality of LEDs;
    control circuitry including at least one of (i) a current source controller tat controls a current supplied to said plurality of LEDs and (ii) a charge pump that ensures a supply voltage to said plurality of LEDs that exceeds a forward voltage of said plurality of LEDs, when the voltage provided by the one or more batteries falls below the forward voltage; and
    a support structure that supports said plurality of LEDs so that the plurality of LEDs extends vertically from an uppermost surface of said support structure, the support structure also supporting said receptacle and said control circuitry, and said support structure further including a diffuser that diffuses the flickering light emitted by said plurality of LEDs;
    wherein a container mount supported by the support structure fits within a substantially U-shaped opening in a protrusion disposed on an end of a replaceable container having a volatile active to attach the replaceable container to the support structure.

16. The flameless candle according to claim 15, wherein the current source controller includes at least one of a constant current source that supplies a constant current to said plurality of LEDs and a constant average current source that supplies a constant average current to said plurality of LEDs.

17. The flameless candle according to claim 16, wherein the constant average current source alternates application of a current to said plurality of LEDs and the charge pump over the course of a cycle, wherein in one portion of the cycle, current is supplied to said plurality of LEDs, and in another portion of the cycle, a current is supplied only to the charge pump, when the charge pump is operational.

18. The flameless candle according to claim 17, wherein plurality of LEDs consists of a first LED and a second LED, and wherein, concerning the first LED, the second LED and the charge pump, the constant average current source supplies (i) a current only to the first LED for a first portion of the cycle, (ii) a current only to the second LED for a second portion of the cycle, and (iii) a current only to the charge pump, when the charge pump is operational, for a third portion of the cycle.

19. The flameless candle according to claim 15, wherein the predetermined forward voltage is between approximately 1.8 and approximately 2.5 volts.

20. The flameless candle according to claim 15, wherein said control circuitry comprises automatic shut-off means to shut off said plurality of LEDs after a predetermined time period.

21. The flameless candle according to claim 15, wherein said support structure comprises a chassis and a holder removably attachable to the chassis.

22. The flameless candle according to claim 21, wherein the holder is removably attachable for replacement of the holder with another holder.

23. The flameless candle according to claim 15, further comprising an outer shell extending above a height of said plurality of LEDs.

24. The flameless candle according to claim 15, further comprising an outer shell spaced from and containing said container mount and said plurality of LEDs.

25. A flameless candle for releasing a volatile active, said candle comprising:
    a plurality of LEDs that emit a flickering light that emulates a flame of a candle;
    a support structure comprising a light diffusing portion, said plurality of LEDs being supported by said support structure to extend vertically from an uppermost surface of said support structure such that the flickering light is diffused by the light diffusing portion; and
    a mount supported by said support structure for mounting a replaceable container including a volatile active,
    wherein the mount includes a post and the replaceable container includes a protrusion disposed on an end thereof, and wherein the replaceable container is inserted upwardly through a bottom of the support structure or horizontally through a side of the support structure so that the post fits within the protrusion of the replaceable container to attach the replaceable container to the support structure.

26. The flameless candle according to claim 25, wherein the support structure includes a first aperture arranged proximate to the bottom thereof for allowing air to enter said support structure and a second aperture arranged proximate to a top of said support structure, thereby allowing convective air flow within the support structure between the first aperture and the second aperture.

27. The flameless candle according to claim 26, further comprising an adjustable vent that adjusts to adjust the air flow between the first aperture and the second aperture.

28. The flameless candle according to claim 25, wherein said support structure comprises a replaceable holder including the light diffusing portion.

29. The flameless candle according to claim 25, further comprising an outer shell extending above a height of said plurality of LEDs.

30. The flameless candle according to claim 25, further comprising an outer shell spaced from and containing said mount and said plurality of LEDs.

* * * * *

UNITED STATES PATENT AND TRADEMARK OFFICE
CERTIFICATE OF CORRECTION

PATENT NO. : 7,503,668 B2 Page 1 of 1
APPLICATION NO. : 11/050242
DATED : March 17, 2009
INVENTOR(S) : Jose Porchia et al.

It is certified that error appears in the above-identified patent and that said Letters Patent is hereby corrected as shown below:

Column 17, Line 46: replace "On" with --on--

Column 17, Line 64: replace "trough" with --through--

Column 18, Line 39: replace "tat" with --that--

Signed and Sealed this

Fifth Day of May, 2009

JOHN DOLL
*Acting Director of the United States Patent and Trademark Office*